(12) United States Patent
Martellaro et al.

(10) Patent No.: US 9,667,884 B2
(45) Date of Patent: May 30, 2017

(54) SYSTEM AND METHOD FOR EVALUATING SURGICAL KNOT FORMATION

(71) Applicant: LSI Solutions, Inc., Victor, NY (US)

(72) Inventors: Angelo John Martellaro, Shortsville, NY (US); Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 510 days.

(21) Appl. No.: 14/478,819

(22) Filed: Sep. 5, 2014

(65) Prior Publication Data

US 2016/0069761 A1    Mar. 10, 2016

(51) Int. Cl.

| G01L 5/04 | (2006.01) |
|---|---|
| G06T 7/00 | (2017.01) |
| G06T 7/20 | (2017.01) |
| H04N 5/247 | (2006.01) |
| G01L 5/10 | (2006.01) |
| A61B 17/06 | (2006.01) |
| G09B 23/28 | (2006.01) |
| A61B 17/00 | (2006.01) |
| A61B 90/00 | (2016.01) |

(52) U.S. Cl.
CPC ....... *H04N 5/247* (2013.01); *A61B 17/06166* (2013.01); *G01L 5/101* (2013.01); *G09B 23/28* (2013.01); *A61B 2017/00725* (2013.01); *A61B 2090/064* (2016.02)

(58) Field of Classification Search
CPC ... G01L 5/101; G09B 23/28; A61B 2090/064; A61B 17/06166; A61B 2017/00725; H04N 5/247
USPC ........ 702/138; 434/262, 273, 274, 272, 258, 434/267, 260; 623/2.12, 904; 606/232, 606/144, 145; 289/1.5, 13, 17, 2, 18.1
See application file for complete search history.

(56) References Cited

U.S. PATENT DOCUMENTS

| 3,775,865 A | 12/1973 | Rowan |
| 4,321,047 A | 3/1982 | Landis |
| 4,734,034 A | 3/1988 | Maness |
| (Continued) | | |

FOREIGN PATENT DOCUMENTS

EP    0870292    7/2008

OTHER PUBLICATIONS

May 31, 1999 http://www.ncbi.nlm.nih.gov/pubmed/10376458; Gallagher, A , Virtual Reality Training in Laparoscopic Surgery: A Preliminary Assessment of Minimally Invasive Surgical Trainer Virtual Reality Mist VR.
Jan. 1, 2006 http://www.ncbi.nlm.nih.gov/pubmed/16709348#; Rosser, JC , The Use of a "Hybrid" Trainer in an Established Laparoscopic Skills Program.
Oct. 9, 2006 http://citeseerx.ist.psu.edu/viewdoc/similar?doi=10.1.1.218.3399&type=sc; Mayer, Hermann , A System for Robotic Heart Surgery That Learns to Tie Knots Using Recurrent Neutral Networks.

(Continued)

*Primary Examiner* — Carol S Tsai
(74) *Attorney, Agent, or Firm* — Christopher B. Miller

(57) ABSTRACT

A system for evaluating surgical knot formation is disclosed. The system includes a first surgically relevant object, a pressure sensor, and at least one pair of suture ends passing through the pressure sensor and the first surgically relevant object. The system also includes a controller coupled to the pressure sensor and configured to 1) transform signals from the pressure sensor into a pressure map having pressure magnitudes from a plurality of locations on the pressure sensor corresponding to one or more knots which may be formed in the at least one pair of suture ends; and 2) format the pressure map for display.

37 Claims, 16 Drawing Sheets

(56) References Cited

U.S. PATENT DOCUMENTS

| | | | | |
|---|---|---|---|---|
| 5,425,949 | A * | 6/1995 | Bennett | A61L 17/145 424/426 |
| 5,543,218 | A * | 8/1996 | Bennett | A61L 17/08 424/422 |
| 5,716,376 | A * | 2/1998 | Roby | A61B 17/06166 606/228 |
| 6,398,557 | B1 * | 6/2002 | Hoballah | G09B 23/28 434/262 |
| 6,412,833 | B2 | 7/2002 | Lusk | |
| 6,770,084 | B1 | 8/2004 | Bain | |
| 8,323,032 | B2 | 12/2012 | Deering | |
| 8,388,351 | B2 | 3/2013 | Potti Cuervo | |
| 8,398,680 | B2 * | 3/2013 | Sauer | A61B 17/0487 606/232 |
| 8,956,165 | B2 * | 2/2015 | Kurenov | G09B 23/285 434/262 |
| 2001/0030423 | A1 | 10/2001 | Lusk | |
| 2003/0120341 | A1 * | 6/2003 | Shennib | A61B 5/0215 623/2.12 |
| 2004/0142314 | A1 | 7/2004 | Hasson | |
| 2006/0252019 | A1 * | 11/2006 | Burkitt | G09B 23/28 434/262 |
| 2007/0166682 | A1 | 7/2007 | Yarin | |
| 2008/0265576 | A1 | 10/2008 | May-Newman | |
| 2010/0156101 | A1 | 6/2010 | Baldwin | |
| 2011/0160561 | A1 * | 6/2011 | Hastings | A61B 3/165 600/398 |
| 2011/0251641 | A1 * | 10/2011 | Sauer | A61B 17/0487 606/230 |
| 2011/0278842 | A1 | 11/2011 | Spilbor | |
| 2012/0016383 | A1 * | 1/2012 | Sauer | A61B 17/0057 606/144 |
| 2013/0041387 | A1 * | 2/2013 | Skinlo | A61B 17/0469 606/145 |
| 2014/0163664 | A1 * | 6/2014 | Goldsmith | A61B 17/00491 623/1.11 |

OTHER PUBLICATIONS

Dec. 21, 2006 http://www.nejum.org/doi/full/10.1056/NEJMra054785; Reznick, Richard K., Teaching Surgical Skills—Changes in the Wind.

Jan. 1, 2008 http://www.covidien.com/imageServer.aspx?contentID=11850&contenttype=application/pdf; Edlich, Richard , Surgical Knot Tying Manual Third Edition.

Jul. 10, 2008 http://oslovet.norecopa.no/PRODUKT.ASPX?PRODUKT=5447; Norecopa Knot Tying Trainer.

Oct. 28, 2011 http://ieeexplore.ieee.org/xpl/articleDetails.jsp?tp=&arnumber=6127005&queryText%3Dbiocompatible+polymeric+wireless; Xue, Ning , Biocompatible Polymeric Wireless Pressure Sensor for Intraocular Pressure Sensing Application.

Feb. 1, 2012 https://interventions.onlinejacc.org/article.aspx?articleid=1207195; Rihal, Charanjit , Principles of Percutaneous Paravalvular Leak Closure.

Jan. 14, 2014 Journal of Medical Education 2014, vol. 18, Issue 1, pp. 23-32; Chang, Chih-Hsun , Introduction of a Web-Based Arthroscopic Knot-Tying Training System.

Jun. 13, 2014 Symposium; Lee, Candice Y., Abstract Submission to STS: Prosthetic Aortic Valve Fixation Study.

Aug. 29, 2014 http://limbsandthings.com/uk/products/knot-tying-trainer; Limbs and Things Knot Tying Trainer.

Aug. 29, 2014 http://simulab.com/product/surgery/laparoscopic/laptrainer-simuvision; Laptrainer With Simuvision.

Sep. 2, 2014 http://tekscan.com/video-synchronization; Tekscan Video Synchronization.

Oct. 11, 2014 Symposium; Martellaro, Angelo J., Abstract Submission Presented At the 28th EACTS Annual Meeting: A New Pressure Mapping System Towards Optimizing Cardiac Prostetic Attachment.

Oct. 11, 2014 Symposium; Wong, Joshua , Abstract Submission Presented At the 28th EACTS Annual Meeting: A Novel Knot Tying Training Simulator Providing Real-Time Pressure Sensor Feedback.

* cited by examiner

SYSTEM AND METHOD FOR EVALUATING SURGICAL KNOT FORMATION

FIELD

The claimed invention relates to surgical knot formation, and more specifically to a system and method for evaluating surgical knot formation in training and real-life situations.

BACKGROUND

Tying knots to reliably secure suture is a fundamental skill that students of surgery need to master to become competent surgeons. Knots are needed, for example, for wound closure and attachment of many replacement prosthetic devices, such as, but not limited to replacement aortic valves. Unfortunately, the current ability to assess knot strength and provide feedback to trainees regarding their knot-tying technique is largely subjective. Furthermore, such critique is routinely provided in the operating room environment, which may be ill-suited for objective assessment of a trainee's performance. Even among some surgeons, there is a concern that their knot construction is not optimal.

Optimal knot construction can depend on a variety of factors. When hand-tying knots, for example, a choreographed sequence of suture manipulations must occur in proper order. Appropriate suture tension, which can vary depending on the type of suture being used and/or the type of tissue being sutured, must be maintained throughout the knot formation. As one example, the amount of tension applied by the surgeon to the final "tails" (i.e. free ends of the suture) of a knot significantly alters the degree of slippage, with approximately 80% of the break strength of the suture being preferred during this final step in knot formation. In addition to the magnitude of this applied tension during knot formation, the rate of tension application is also important. For example, a knot's breakage strength is significantly influenced by the rate of application of forces to the tails of the knot. When constant force is applied slowly to the tails of the knot, the resultant knot breakage force tends to be significantly higher than for knots for which the same constant force is applied rapidly to the tails. These, as well as other aspects, are all elements of successful, reliable surgical knot tying for which experience and repetition are needed. Unfortunately, it can be difficult to obtain realistic, objective surgical knot tying experience inside or outside of the operating room.

Further complicating this situation is the increasing prevalence of minimally invasive surgical procedures where tool-augmented hand-tying procedures and minimally invasive instruments are often needed to form knots at surgical sites within a patient, remote from the surgeon. For example, many patients undergo aortic valve replacement surgery. This surgery often involves the need to suture (with accompanying knots) a sewing ring for the prosthetic aortic valve into the aortic root tissue of the patient's heart. If each knotted suture is not tensioned sufficiently, and substantially evenly, then there may be an increased risk of paravalvular leak (PVL). PVL occurs external to the prosthetic valve at the interface between the sewing ring and the underlying cardiac tissue annulus. Even small paravalvular leaks maybe associated with significant morbidity, such as intravascular hemolysis (breakage of a red blood cell's membrane) and anemia as red blood cells are forced through a narrow orifice at very high velocities, and increased risk of death.

PVL affects 5% to 17% of all surgically implanted heart valves. Reoperation is associated with increased morbidity and is not always successful because of underlying tissue breakdown, inflammation, or calcification. Although this is just one surgical example, it is notably very desirable that risk factors contributing to poor surgical procedure outcomes are minimized, and one way to contribute to this goal would be to help surgeons and surgeons-in-training to improve their knot tying skills.

Therefore, it would be very beneficial to have a reliable, reusable, and objective system and method for evaluating surgical knot formation, as well as the formation of multiple inter-related knots (as in the case of an aortic valve replacement), that could effectively be implemented with surgical simulation materials to provide training and teaching opportunities outside of an actual operating room environment.

SUMMARY

A system for evaluating surgical knot formation is disclosed. The system includes a first surgically relevant object, a pressure sensor, and at least one pair of suture ends passing through the pressure sensor and the first surgically relevant object. The system also includes a controller coupled to the pressure sensor and configured to 1) transform signals from the pressure sensor into a pressure map having pressure magnitudes from a plurality of locations on the pressure sensor corresponding to one or more knots which may be formed in the at least one pair of suture ends; and 2) format the pressure map for display.

Another system for evaluating surgical knot formation is disclosed. The system includes a pressure sensor configured to be held in conjunction with a first surgically relevant object and/or a second surgically relevant object by: 1) passage of at least one pair of suture ends through the pressure sensor and the first surgically relevant object; or 2) passage of the at least one pair of suture ends through the second surgically relevant object, the pressure sensor, and the first surgically relevant object. The system also includes a controller coupled to the pressure sensor and configured to: 1) transform signals from the pressure sensor into a pressure map having pressure magnitudes from a plurality of locations on the pressure sensor corresponding to one or more knots which may be formed in the at least one pair of suture ends; and 2) format the pressure map for display.

A method for evaluating surgical knot formation is further disclosed. One or more knots are formed in each of one or more pairs of suture ends which have been passed through at least one surgically relevant object and a pressure sensor. Using a controller, signals from the pressure sensor are transformed into a pressure map having pressure magnitudes from a plurality of locations on the pressure sensor corresponding to the one or more or more knots. The pressure map is displayed on a user interface.

BRIEF DESCRIPTION OF THE DRAWINGS

FIG. 6A-2 is an enlarged view of a portion of the device from FIG. 6A-1 showing a cross-section of the one or more surgically relevant objects and the pressure sensor in more detail.

FIG. 6B-1 is a partial cross-sectional side view of the frame from FIG. 6A-1 with the clamp positioned to hold the sutures in place behind the one or more surgically relevant objects and the pressure sensor while a mechanical knot is applied to the suture ends by a minimally invasive fastening device.

FIG. 6B-2 schematically illustrates one embodiment of a three-dimensional (3D) pressure map associated with a location where the mechanical knot is being placed against one of the surgically relevant objects from FIG. 6B-1.

FIG. 6C-1 is a partial cross-sectional side view of the frame from FIG. 6B-1 with the minimally invasive fastening device removed after a mechanical fastener has been applied to the suture ends.

FIG. 6C-2 schematically illustrates one embodiment of a 3D pressure map associated with the location where the mechanical knot was placed against the surgically relevant objects as shown in FIG. 6C-1.

Figure 1A:
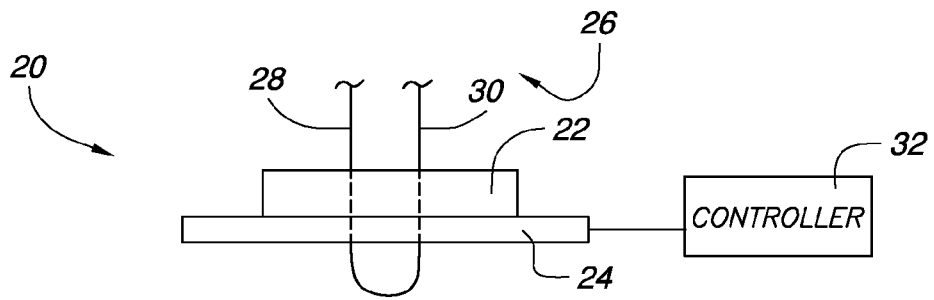
FIGS. 1A-1G schematically illustrate different embodiment of a system for evaluating surgical knot formation.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A schematically illustrates one embodiment of a system 20 for evaluating surgical knot formation. The system 20 includes a first surgically relevant object 22 and a pressure sensor 24. The first surgically relevant object 22 is an object on which it is desired to form a suture knot. As non-limiting examples, the first surgically relevant object 22 may include a synthetic tissue, a natural tissue, or a cardiac prosthesis, such as a replacement heart valve or a sewing band or ring.

The first surgically relevant object 22 is preferably mounted in contact with the pressure sensor 24, although some embodiments may provide one or more intermediate materials, such as, but not limited to a cellophane layer to protect or insulate the pressure sensor 24 from the first surgically relevant object 22. One example of a suitable pressure sensor 24 includes, but is not limited to, the Tekscan® pressure sensor model number 5027-100.

In system 20, at least one pair of suture ends 26 passes through the pressure sensor 24 and the first surgically relevant object 22. In this embodiment, the pair of suture ends 26 includes a first suture end 28 and a second suture end 30 which are different ends of the same suture. The suture of system 20 loops behind the pressure sensor 24 such that when a knot (not shown) is formed using the first and second suture ends 28, 30 against the first surgically relevant object 22, the knot will tend to apply a pressure through the first surgically relevant object 22 which can be sensed by the pressure sensor 24.

The system 20 also has a controller 32 coupled to the pressure sensor 24 and configured to 1) transform signals from the pressure sensor 24 into a pressure map having pressure magnitudes from a plurality of locations on the pressure sensor 24 corresponding to one or more knots which may be formed in the at least one pair of suture ends 26; and 2) format the pressure map for display. The controller 32 may comprise a computer, laptop, microprocessor, application specific integrated circuit (ASIC), field programmable gate array (FPGA), digital components, analog components, or any combination and/or plurality thereof, whether localized or distributed. The controller 32 may also be configured to execute machine readable instructions which are stored on a non-transitory computer readable medium such as, but not limited to, a compact disc (CD), a magnetic tape, an optical drive, a digital versatile disc (DVD), a hard drive, a Blu-ray disc, a flash drive, a thumb drive, a memory card, or a memory chip.

Although a system for evaluating surgical knot formation, such as system 20, can be used with a single surgically relevant object, it is preferred that such systems use or work with at least a first and a second surgically relevant object. Such scenarios are more realistic. For example, two sides of an open wound might need to be sutured together, or a replacement heart valve might need to be sutured to existing tissue in a patient. In these, and in other cases, a knotting tension can be more realistically modelled or simulated when both surgically relevant objects are incorporated. Accordingly, the remaining embodiments in this specification will include first and second surgically relevant objects.

Figure 1B:
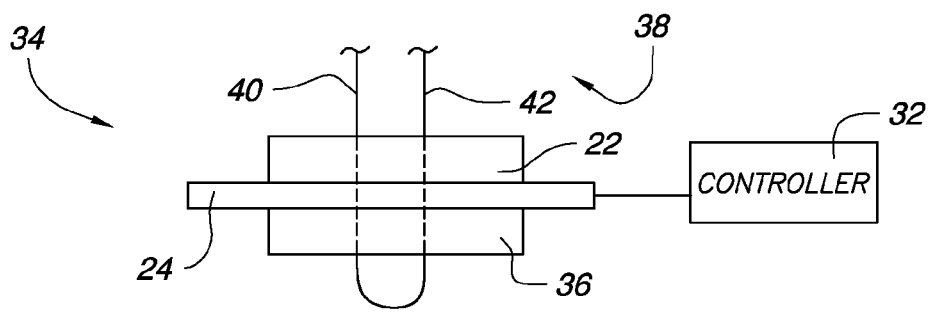

FIG. 1B schematically illustrates another embodiment of a system 34 for evaluating surgical knot formation. The system 34 includes a first surgically relevant object 22 and a pressure sensor 24. The first surgically relevant object 22 is an object on which it is desired to form a suture knot. As mentioned previously, some non-limiting examples of the first surgically relevant object 22 may include a synthetic tissue, a natural tissue, or a cardiac prosthesis, such as a replacement heart valve or a sewing band or ring. The system 34 also includes a second surgically relevant object 36. The second surgically relevant object 36 is an object to which it is desired to attach the first surgically relevant object 22. Some non-limiting examples of a second surgically relevant object 36 may include synthetic tissue, natural tissue, and an aortic root model.

In the embodiment of system 34, the first surgically relevant object 22 is preferably mounted in contact with a first side of pressure sensor 24, although some embodiments may provide one or more intermediate materials, such as, but not limited to a cellophane layer to protect or insulate the pressure sensor 24 from the first surgically relevant object 22. Similarly, the second surgically relevant object 36 is preferably mounted in contact with a second side of pressure sensor 24, opposite the first side, although some embodiments may provide one or more intermediate materials, for example for protection or insulation as described above. Still other embodiments may orient the second surgically relevant object 36 between the first surgically relevant object 22 and the pressure sensor. Such embodiments may allow a more realistic interface between the two surgically relevant objects 22, 36 while still providing pressure information. For simplicity, however, the remaining embodiments discussed herein will have the pressure sensor 24 mounted between the first and second surgically relevant objects 22, 36. A suitable example of a pressure sensor 24 has been discussed above.

In system 34, at least one pair of suture ends 38 passes through the second surgically relevant object 36, the pressure sensor 24, and the first surgically relevant object 22. In this embodiment, the pair of suture ends 38 includes a first suture end 40 and a second suture end 42 which are different ends of the same suture. The suture of system 34 loops behind the second surgically relevant object 36 such that when a knot (not shown) is formed using the first and second suture ends 40, 42 against the first surgically relevant object 22, the knot will tend to compress the first and second surgically relevant objects 22, 36 against the pressure sensor 24, thereby creating a pressure which can be sensed by the pressure sensor 24.

The system 34 also has a controller 32 coupled to the pressure sensor 24 and configured to 1) transform signals from the pressure sensor 24 into a pressure map having pressure magnitudes from a plurality of locations on the pressure sensor 24 corresponding to one or more knots which may be formed in the at least one pair of suture ends 26; and 2) format the pressure map for display.

Figure 1C:
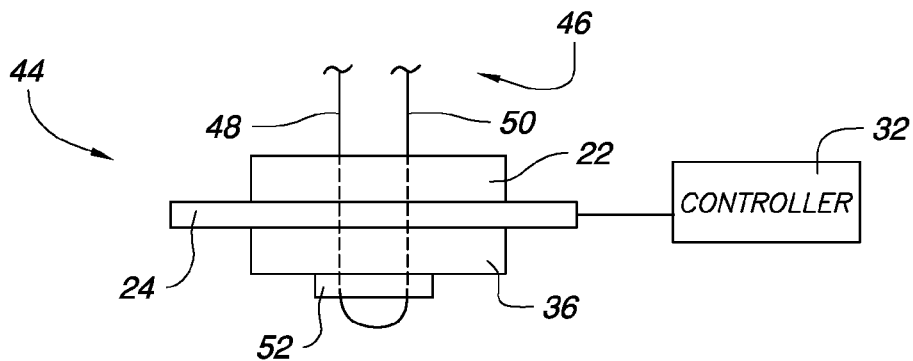

FIG. 1C schematically illustrates another embodiment of a system 44 for evaluating surgical knot formation. The system 44 includes a first surgically relevant object 22, a pressure sensor 24, and a second surgically relevant object 36, the features of which have been discussed above. This embodiment also has a pledget 52 located on a side of the second surgically relevant object 36 away from the pressure sensor 24.

In system 44, at least one pair of suture ends 46 passes through the pledget 52, the second surgically relevant object 36, the pressure sensor 24, and the first surgically relevant object 22. In this embodiment, the pair of suture ends 46 includes a first suture end 48 and a second suture end 50 which are different ends of the same suture. The suture of system 44 loops behind the pledget 52 such that when a knot (not shown) is formed using the first and second suture ends 48, 50 against the first surgically relevant object 22, the knot will tend to compress the first and second surgically relevant objects 22, 36 against the pressure sensor 24, thereby creating a pressure which can be sensed by the pressure sensor 24. The system 34 also has a controller 32, the features of which have been discussed above.

Figure 1D:
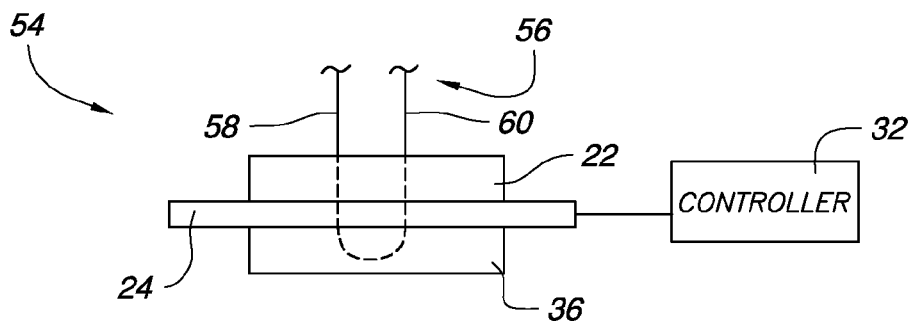

FIG. 1D schematically illustrates another embodiment of a system 54 for evaluating surgical knot formation. The system 54 includes a first surgically relevant object 22, a pressure sensor 24, and a second surgically relevant object 36, the features of which have been discussed above.

In system 54, at least one pair of suture ends 56 passes through the second surgically relevant object 36, the pressure sensor 24, and the first surgically relevant object 22. In this embodiment, the suture only exits the second surgically relevant object 36 on one side of the object 36. The pair of suture ends 56 includes a first suture end 58 and a second suture end 60 which are different ends of the same suture. The suture of system 54 loops within the second surgically relevant object 36 such that when a knot (not shown) is formed using the first and second suture ends 58, 60 against the first surgically relevant object 22, the knot will tend to compress the first and second surgically relevant objects 22, 36 against the pressure sensor 24, thereby creating a pressure which can be sensed by the pressure sensor 24. The system 34 also has a controller 32, the features of which have been discussed above.

Figure 1E:
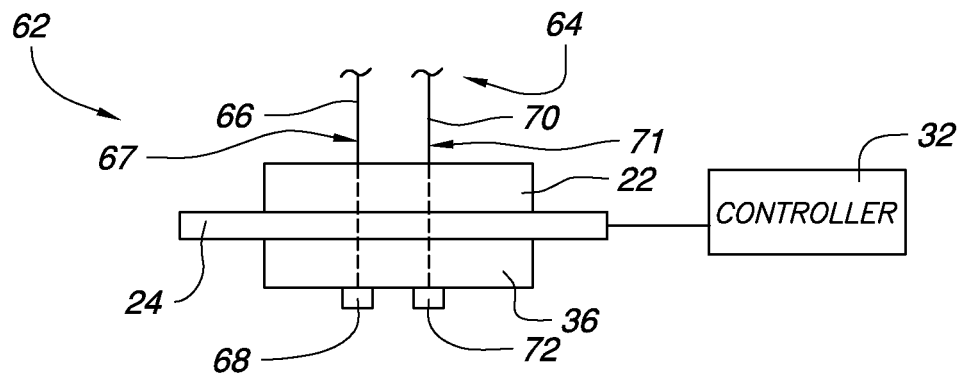

FIG. 1E schematically illustrates another embodiment of a system 62 for evaluating surgical knot formation. The system 62 includes a first surgically relevant object 22, a pressure sensor 24, and a second surgically relevant object 36, the features of which have been discussed above.

In system 62, at least one pair of suture ends 64 passes through the second surgically relevant object 36, the pressure sensor 24, and the first surgically relevant object 22. In this embodiment, the pair of suture ends 64 includes a first suture end 66 and a second suture end 70. The first suture end 66 is a first end of a first suture 67, while the second suture end 70 is a first suture end of a second, separate suture 71. The first suture 67 has a second end having an anchor 68. Similarly, the second suture 71 has a second end having an anchor 72. The anchors 68, 72 are behind the second surgically relevant object 36 such that when a knot (not shown) is formed using the first and second suture ends 66, 70 against the first surgically relevant object 22, the knot will tend to compress the first and second surgically relevant objects 22, 36 against the pressure sensor 24, thereby creating a pressure which can be sensed by the pressure sensor 24. The system 62 also has a controller 32, the features of which have been discussed above.

Figure 1F:
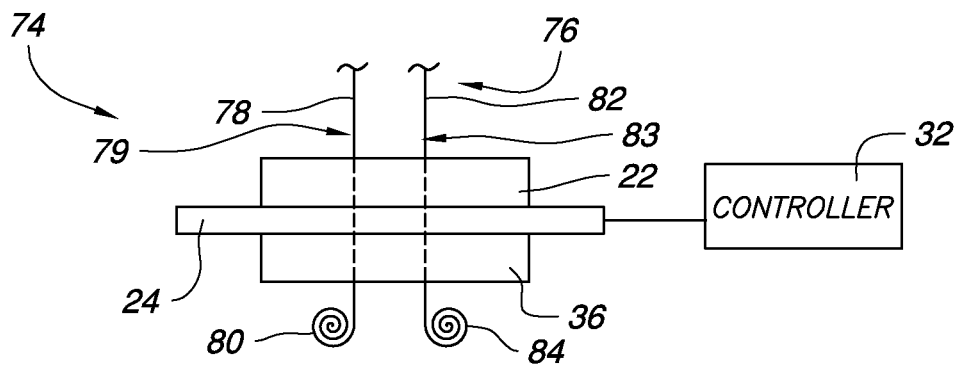

FIG. 1F schematically illustrates another embodiment of a system 74 for evaluating surgical knot formation. The system 74 includes a first surgically relevant object 22, a pressure sensor 24, and a second surgically relevant object 36, the features of which have been discussed above.

In system 74, at least one pair of suture ends 76 passes through the second surgically relevant object 36, the pressure sensor 24, and the first surgically relevant object 22. In this embodiment, the pair of suture ends 76 includes a first suture end 78 and a second suture end 82. The first suture end 78 is a first end of a first suture 79, while the second suture end 82 is a first suture end of a second, separate suture 83. The first suture 79 has a second end wrapped around a first spool 80. Similarly, the second suture 83 has a second end wrapped around a second spool 84. The first and second spools 80, 84 are selectively lockable to prevent rotation of the spools and payout of the first and second sutures 79, 83 while locked.

Since the first and second suture ends 78, 82 are not part of the same suture in the embodied system 74, and since there is no anchor or loop coupling sutures to either the second surgically relevant object 36, the pressure sensor 24, or the first surgically relevant object 22, the system should include some form of support to hold the second surgically relevant object 36 in place so that a knot formed (not shown) using the first and second suture ends 78, 82 against the first surgically relevant object 22 will tend to compress the first and second surgically relevant objects 22, 36 against the pressure sensor 24, thereby creating a pressure which can be sensed by the pressure sensor 24. The system 74 also has a controller 32, the features of which have been discussed above.

Figure 1G:
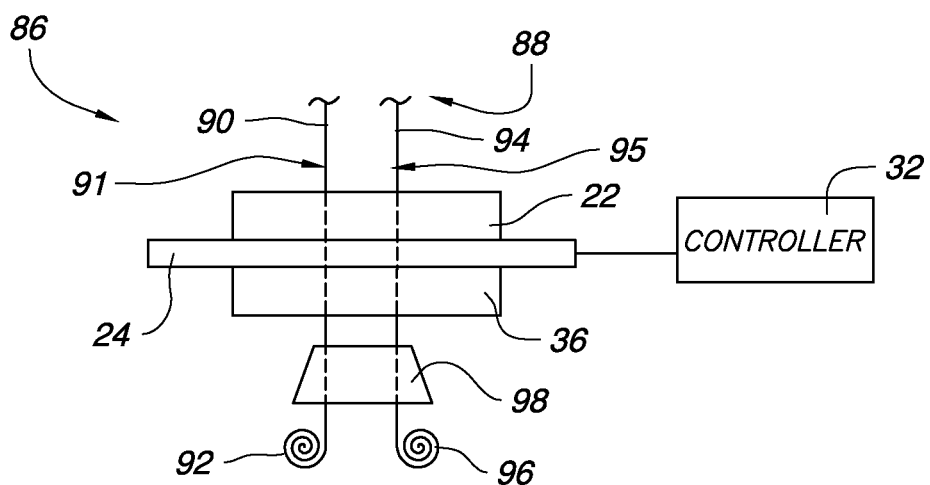

FIG. 1G schematically illustrates another embodiment of a system 86 for evaluating surgical knot formation. The system 86 includes a first surgically relevant object 22, a pressure sensor 24, and a second surgically relevant object 36, the features of which have been discussed above.

In system 86, at least one pair of suture ends 88 passes through the second surgically relevant object 36, the pressure sensor 24, and the first surgically relevant object 22. In this embodiment, the pair of suture ends 88 includes a first suture end 90 and a second suture end 94. The first suture end 90 is a first end of a first suture 91, while the second suture end 94 is a first suture end of a second, separate suture 95. The first suture 91 has a second end wrapped around a first spool 92. Similarly, the second suture 95 has a second end wrapped around a second spool 96. In this embodiment, the first and second spools 92, 96 are not lockable, however, the system 86 further includes at least one clamp 98 for selectively locking the second ends of the first and second sutures in place. This prevents payout of the first and second sutures 91, 95 while the clamp 98 is locked.

Since the first and second suture ends 90, 94 are not part of the same suture in the embodied system 86, and since there is no anchor or loop coupling sutures to either the second surgically relevant object 36, the pressure sensor 24, or the first surgically relevant object 22, the system 86 should include some form of support, such as a frame, to hold the second surgically relevant object 36 in place so that a knot formed (not shown) using the first and second suture ends 90, 94 against the first surgically relevant object 22 will tend to compress the first and second surgically relevant objects 22, 36 against the pressure sensor 24, thereby creating a pressure which can be sensed by the pressure sensor 24. The system 86 also has a controller 32, the features of which have been discussed above.

Figure 2:
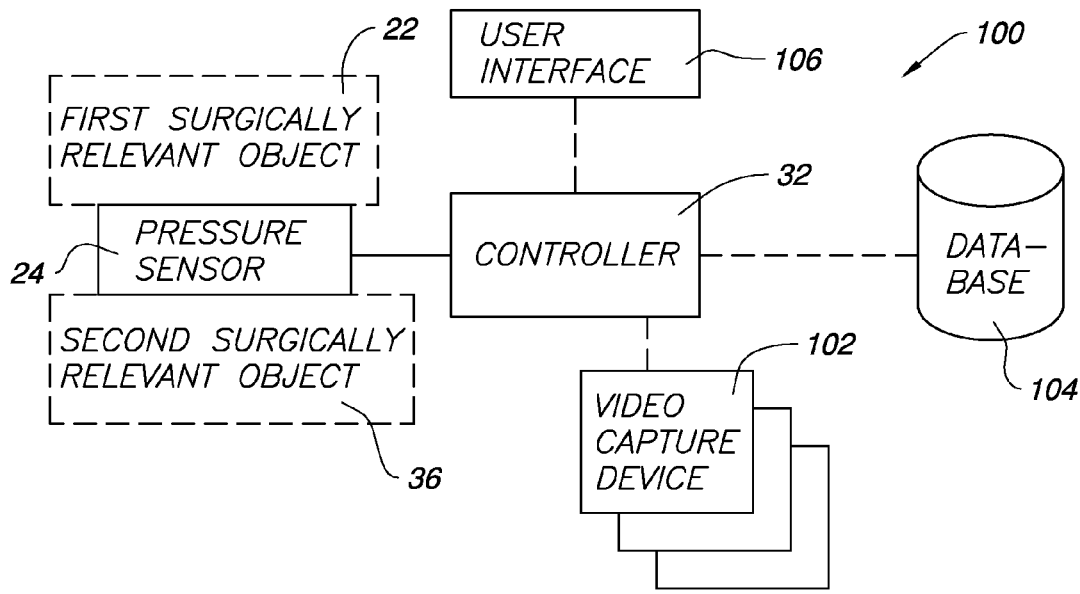
FIG. 2 schematically illustrates another embodiment of a system for evaluating surgical knot formation.

FIG. 2 schematically illustrates another embodiment of a system 100 for evaluating surgical knot formation. The system 100 has a pressure sensor 24 configured to be held in conjunction with a first surgically relevant object 22 and/or a second surgically relevant object 36 by: 1) passage of at least one pair of suture ends through the pressure sensor 24 and the first surgically relevant object 22; or 2) passage of the at least one pair of suture ends through the second surgically relevant object 36, the pressure sensor 24, and the first surgically relevant object 22. The system 100 also has a controller 32 coupled to the pressure sensor 24 and configured to: 1) transform signals from the pressure sensor 24 into a pressure map having pressure magnitudes from a plurality of locations on the pressure sensor 24 corresponding to one or more knots which may be formed in the at least one pair of suture ends; and 2) format the pressure map for display. As with the previous embodiments, the controller 32 may comprise a computer, laptop, microprocessor, application specific integrated circuit (ASIC), field programmable gate array (FPGA), digital components, analog components, or any combination and/or plurality thereof, whether localized or distributed. The controller 32 may also be configured to execute machine readable instructions which are stored on a non-transitory computer readable medium such as, but not limited to, a compact disc (CD), a magnetic tape, an optical drive, a digital versatile disc (DVD), a hard drive, a Blu-ray disc, a flash drive, a thumb drive, a memory card, or a memory chip.

Depending on the embodiment, the controller 32 may be coupled to the pressure sensor 24 by a wired or a wireless connection. For embodiments having a wireless connection, the pressure sensor 24 may derive its power from a separate power supply, or even from a radio frequency (RF)-to-direct current (DC) power source such as an adaptive RF-DC power convertor or the like, such as is known to those skilled in the art, especially in the micro electromechanical systems (MEMS) field. A wireless connection between the pressure sensor 24 and the controller 32 could merely be a convenience or, in some embodiments, a wireless pressure sensor 24, especially one which has a convenient power source, such as an RF-DC power converter, may enable biocompatible pressure sensors to be implanted in a patient's body, for example, in-between a replacement heart valve and a tissue annulus to provide feedback on the formation and/or resultant pressure of the knots holding the two surgically relevant objects together. The pressure data in such a system could also be monitored over time, even after the related surgery has been completed, to look for signs of paravalvular leaks. In still other embodiments, first surgically relevant objects, such as a replacement heart valve sewing ring, could include a built-in biocompatible pressure sensor.

The system 100, of FIG. 2, may optionally have one or more video capture devices 102 coupled to the controller 32. The one or more video capture devices 102 can, as one example, include three different video cameras. The first video camera could be configured, in conjunction with the controller 32, to record a surgeon's hands while his/her hands are directly or indirectly manipulating the at least one pair of suture ends to form a knot against the first surgically relevant object. The actions of the surgeon's hands are highly relevant to the quality of the knots produced, and a corresponding video record can help surgical students and as well as established surgeons to critique their knot tying skills with an eye towards identifying areas for improvement. A second video camera could be configured, in conjunction with the controller 32, to record the surgeon's face as the one or more knots are being formed. Facial expressions can be very helpful in determining a moment where, perhaps, a surgical student consciously or unconsciously recognizes that they may have made an error while tying a knot. A facial video record, as part of a system for evaluating surgical knot formation, can provide some insight into such behaviors or even a helpful indication of a degree of surgical focus by noting how concentrated the surgeon is while forming a surgical knot. A facial video could also provide evidence of knot mastery, for example, in the case where a surgeon is able to produce technically correct knots as indicated by the pressure sensor data while being able to focus on other matters. A third video camera could be configured, in conjunction with the controller 32, to record a knot being formed against the first surgically relevant object.

The system 100 of FIG. 2 may optionally have a database 104 to store and/or provide previously captured pressure data to the controller 32. The database 104 can be as simple as a memory device holding raw data or formatted files, or database 104 can be a complex relational database.

The system 100 may also have a user interface 106. In such embodiments, the controller 32 is further configured to display the pressure map on the user interface 106. As will be discussed in more detail later in this specification, the pressure map may be displayed in a variety of ways, including, but not limited to 1) a two-dimensional pressure map, 2) a three-dimensional pressure map, 3) a time varying two-dimensional pressure map, 4) a time varying three dimensional pressure map, 5) a plot of pressure at a given location corresponding to at least one of the one or more knots as a function of time, and/or 6) as a histogram of intraknot and/or extraknot pressures. Such data, along with one or more substantially synchronized sets of captured video data may be displayed on the user interface 106 in real-time or from previously stored data. Depending on the embodiment, the user interface 106 may also include devices such as a keyboard, a mouse, a touchscreen, and/or another input device to trigger data acquisition, select file names and destinations for data to be saved, enter test information and other parameters, and generally to interact with the system. Such input devices are well-known to those skilled in the art.

Figure 3:
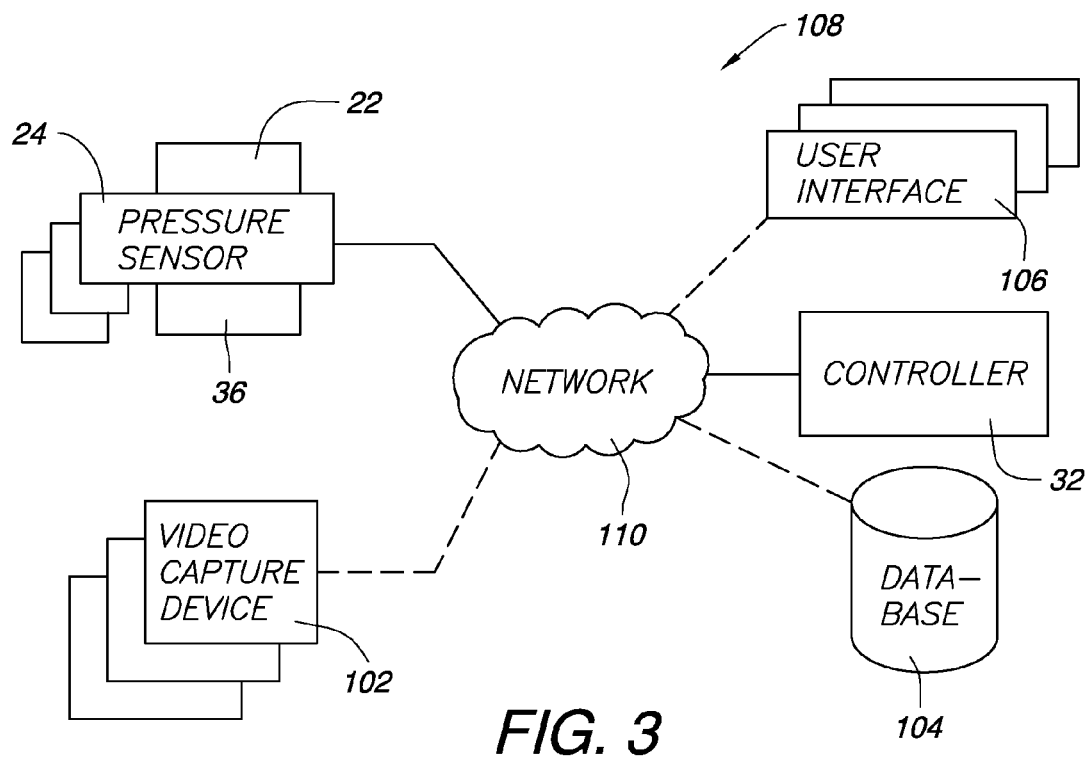
FIG. 3 schematically illustrates a networked embodiment of a system for evaluating surgical knot formation.

FIG. 3 schematically illustrates another embodiment of a system 108 for evaluating surgical knot formation. In this embodiment, the controller 32 is set-up to be a remote controller 32 which is coupled to the remainder of the components (pressure sensor 24, user interface 106, optional video capture device 102, and database 104, discussed previously) over a network 110. The network 110 may be a wired or wireless local area network (LAN or WLAN), or the network may be a wired or wireless wide area network (WAN, WWAN) using any number of communications protocols to pass data back and forth. Having a system 108 where the controller 32 is located remotely allows multiple client side pressure sensors 24 and multiple user interfaces 106 to share the resources of the controller 32. As one example, in such a scenario, the controller 32 could be a suitably programmed web serving host for gathering data from multiple networked pressure sensors 24 and serving pressure map information, as well as optional captured video information to a variety of client user interfaces 106 for display and analysis. Such a system could potentially reduce equipment costs for locations such as medical schools having a need for multiple knot-tying evaluation systems. Such a system might also be very helpful if bio-compatible, implantable pressure sensors 24 are implanted into patients during surgery so that a centralized controller 32 could collect pressure data from a multitude of client pressure sensors 24 for distribution to appropriate user interfaces 106 at corresponding doctor's offices.

Figure 4:
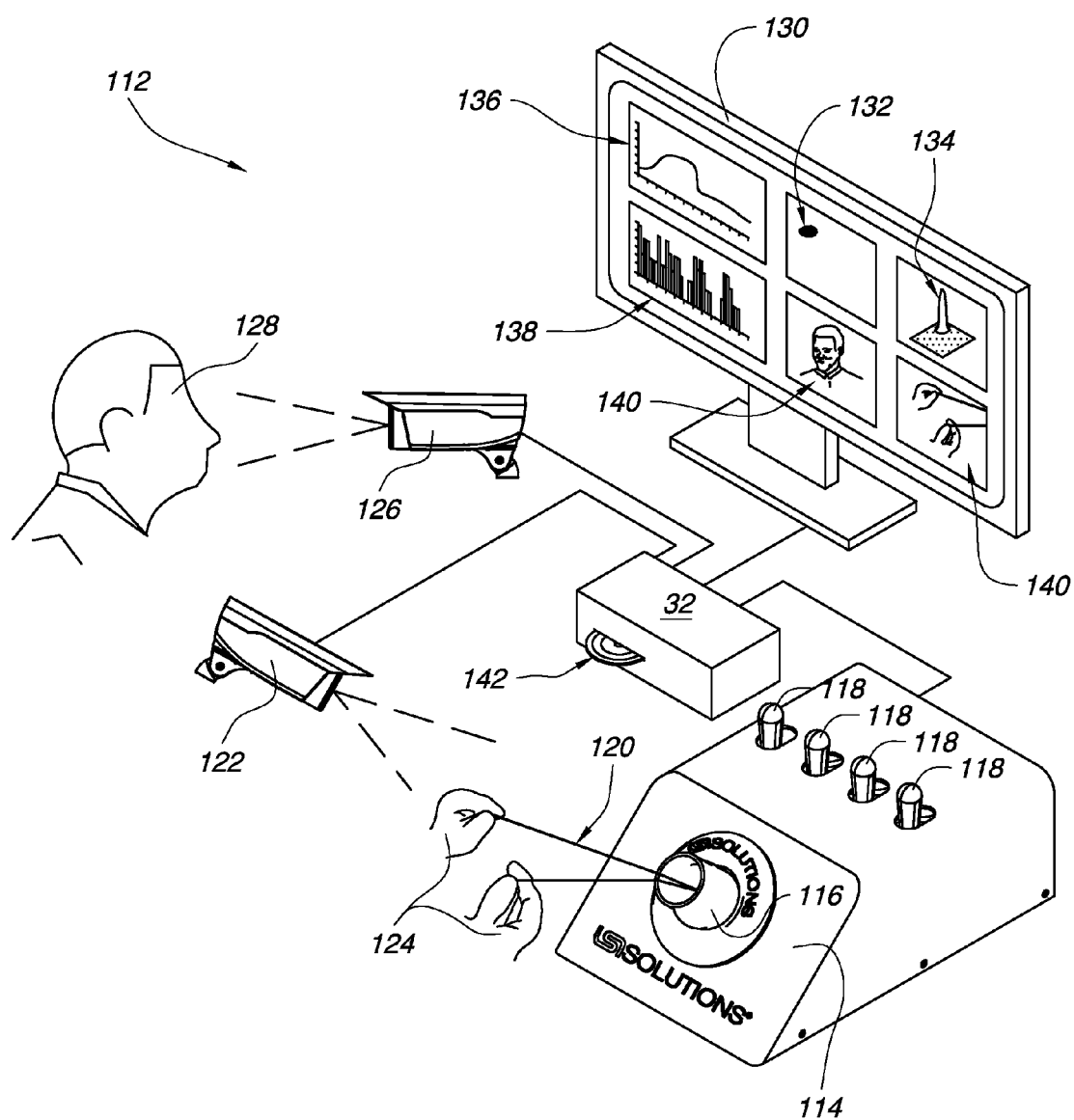
FIG. 4 schematically illustrates a further embodiment of a system for evaluating surgical knot formation.

FIG. 4 schematically illustrates a further embodiment of a system 112 for evaluating surgical knot formation. The system 112 has first and second surgically relevant objects (not visible in this view) supported within a frame 114. In this embodiment, the frame 114 includes a surgical orifice 116 configured to resemble a portion of the ascending aorta. The frame 114 also houses and provides access to suture clamps 118 which will be discussed in more detail later in this specification. Each suture clamp 118 corresponds to a different pair of suture ends which passes through the second surgically relevant object, the pressure sensor, the first surgically relevant object, and then out of the orifice 116. For convenience, however, only one pair of suture ends 120 is illustrated in this view. The pressure sensor (not visible in this view), supported by the frame 114, is coupled to a controller 32. A first video capture device 122 is configured, in conjunction with the controller 32, to record a surgeon's hands 124 while those hands are directly (as illustrated here) or indirectly manipulating the pair of suture ends 120 to form a knot against the first surgically relevant object. The system 112 also has a second video capture device 126 configured to record, in conjunction with the controller 32, the surgeon's face 128. A user interface 130 is also coupled to the controller 32. As non-limiting examples, the user interface 130 could be a computer monitor or television.

In the embodiment of FIG. 4, the controller 32 is configured to transform signals from the pressure sensor into a pressure map having pressure magnitudes from a plurality of locations on the pressure sensor corresponding to one or more knots which may be formed in the at least one pair of suture ends 120. The controller 32 is also configured to format the pressure map for display and to display the pressure map on the user interface 130 along with one or more streams of video data from the video capture devices. As with previous embodiments, the pressure maps may be displayed, among other ways, as a time varying two-dimensional pressure map 132, a time varying three-dimensional pressure map 134, a plot of pressure at a given location corresponding to at least one of the one or more knots as a function of time 136, and as a histogram 138 of intraknot and/or extraknot pressures. The controller 32 is further configured to display the synchronized video scene data from the video capture devices 122, 126 on the user interface 130 as one or more videos 140. Since recorded video frames or data is typically captured at a known frame rate, the video data can be captured as a function of time and displayed in synchronization with the one or more displays 132, 134, 136, 138 of data based on the pressure maps.

In the embodiment of FIG. 4, the controller 32 may also be configured to write data to and/or read data from a portable memory, such as, but not limited to a DVD, Blu-ray disc, flash drive, or CD 142. In addition to being able to write captured data to the portable memory 142 for later retrieval by the system 112, the controller 32 may also be configured to format the captured data as a single video file which includes the combined one or more displays 132, 134, 136, 138 of data based on the pressure maps as well as the one or more video feeds 140 from the video capture devices 122, 126. Such a single video file could be formatted to be played by one or more video decoders on a computer or conventional video playback device so that a person having used the system 112 could leave the system 112 with a copy of their own results that could be viewed almost anywhere. This would be very helpful for students who have to share the system 112 for evaluating surgical knot performance.

Figure 5:
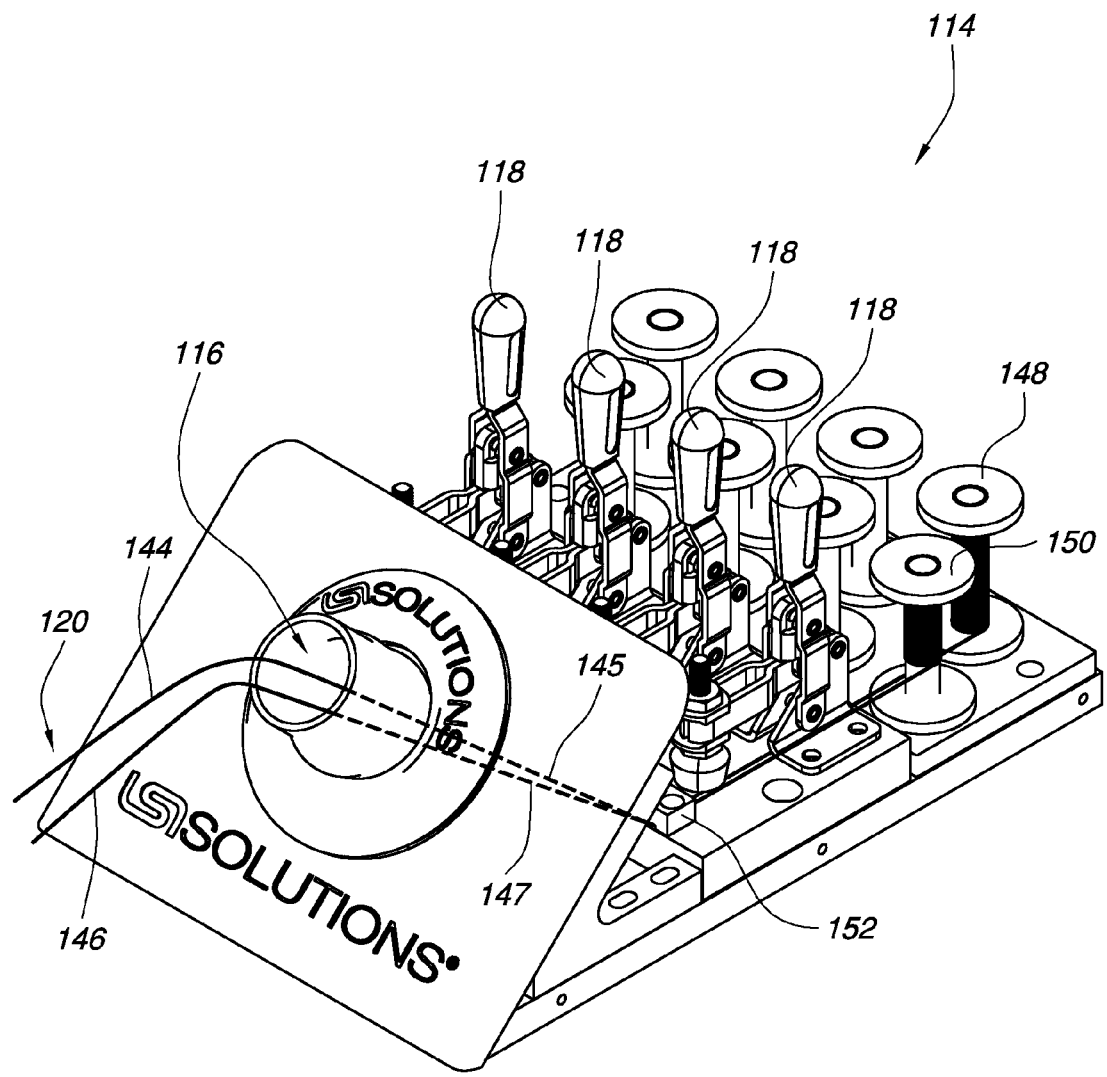
FIG. 5 is a partially exposed perspective view of one embodiment of a frame for supporting one or more surgically relevant objects and a pressure sensor in a system for evaluating surgical knot formation.

FIG. 5 is a partially exposed perspective view of one embodiment of the frame 114 for supporting one or more surgically relevant objects and a pressure sensor in a system for evaluating surgical knot formation. The pressure sensor and surgically relevant objects are still not visible in this view, but they will be in some of the following figures. As mentioned previously, in this embodiment, the frame 114 has a surgical orifice 116 configured to resemble a portion of the ascending aorta. The frame 114 also houses and provides access to suture clamps 118. In this example, there are four suture clamps 118, each clamp 118 corresponding to a different pair of suture ends which pass through the second surgically relevant object, the pressure sensor, and the first surgically relevant object, and then out of the orifice 116. For convenience, only one pair of suture ends 120 is shown and discussed herein, since each pair of suture ends 120 and its corresponding clamp 118 operate similarly. Other embodiments may include a greater or lesser number of suture clamps 118 and corresponding pairs of suture ends 120.

Similar to the embodiment of FIG. 1G discussed above, the pair of suture ends 120 in the embodiment of FIG. 5 includes a first suture end 144 and a second suture end 146. The first suture end 144 is a first end of a first suture 145, while the second suture end 146 is a first suture end of a second, separate suture 147. The first suture 145 has a second end wrapped around a first spool 148. Similarly, the second suture 147 has a second end wrapped around a second spool 150. In this embodiment, the first and second spools 148, 150 are not lockable, however, the frame's 114 suture clamp 118 is operable to selectively lock the second ends of the first and second sutures 145, 147 in place. This prevents payout of the first and second sutures 145, 147 while the clamp 118 is locked. One suitable type of clamp 118 includes, but is not limited to the hold-down toggle clamp, model number 5126A19 available from De-Sta-Co. The sutures 145, 147 pass from their respective spools 148, 150 under the suture clamp 118, through a guide block 152, through the second surgically relevant object, through the pressure sensor, through the first surgically relevant object, and out of the orifice 116.

Figures 1, 6A:
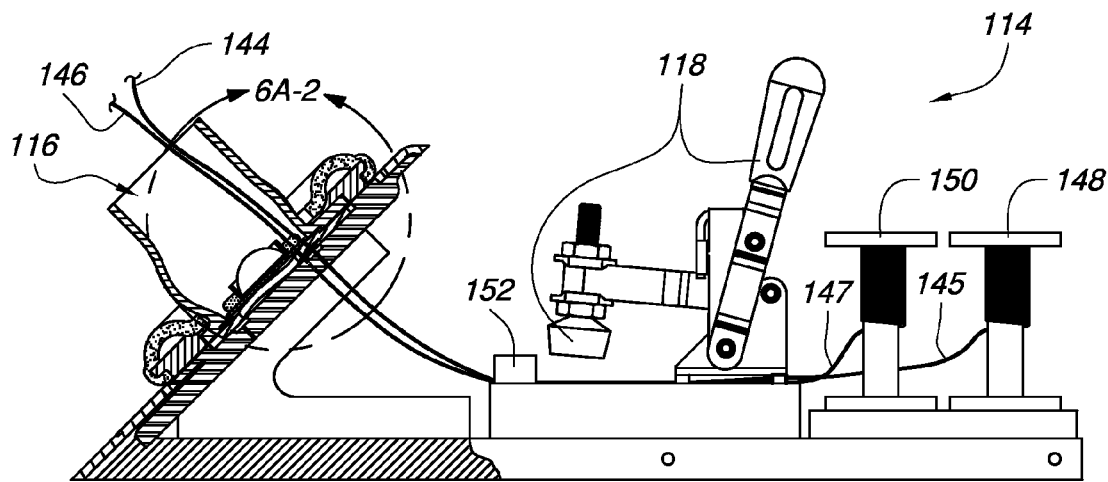
FIG. 6A-1 is a partial cross-sectional side view of a frame for supporting one or more surgically relevant objects and a pressure sensor in a system for evaluating surgical knot formation. A clamp in the device of FIG. 6A-1 is positioned to allow suture to be pulled through the one or more surgically relevant objects and the pressure sensor.
Figures 2, 6A:
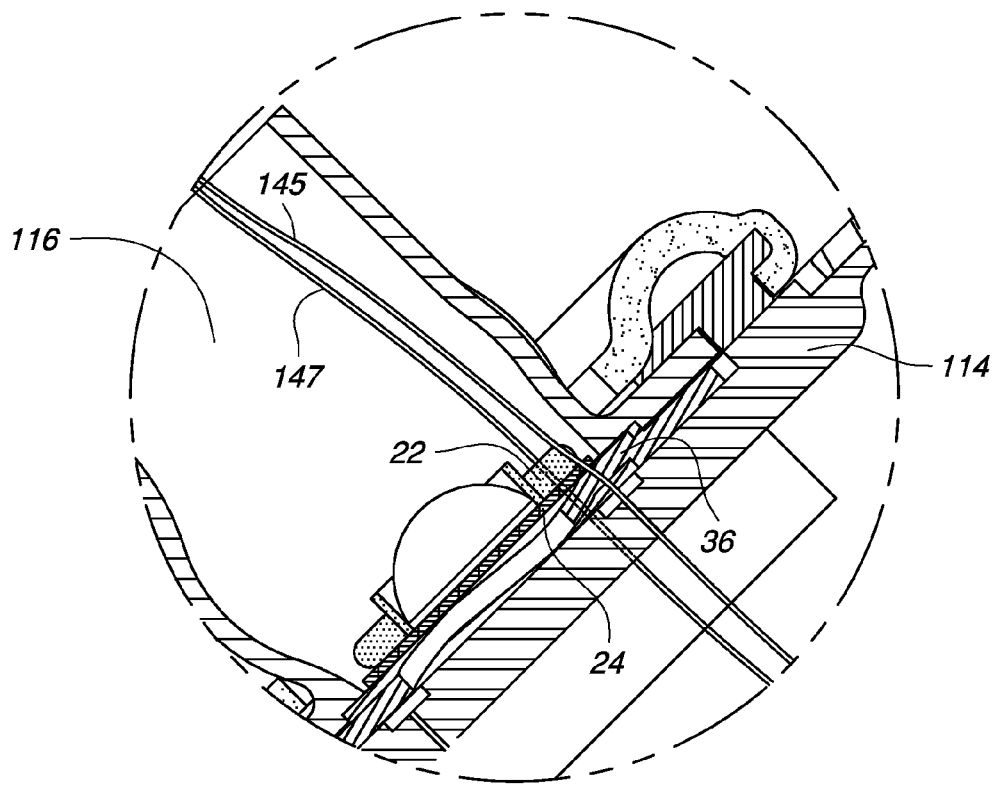

FIG. 6A-1 is a partial cross-sectional side view of the frame 114. FIG. 6A-2 is an enlarged view of a portion of the device from FIG. 6A-1 showing a cross-section of the second surgically relevant object 36, the pressure sensor 24, and the first surgically relevant object 22 as supported by the frame 114. In this example, the first surgically relevant object 22 is the sewing ring of a replacement heart valve, and the second surgically relevant object 36 is a model of an aortic root.

Since the first and second suture ends 144, 146 are not part of the same suture, and since there is no anchor or loop coupling the sutures to either the second surgically relevant object 36, the pressure sensor 24, or the first surgically relevant object 22, the frame 114 is configured to hold the second surgically relevant object 36 in place so that a knot formed (not shown) using the first and second suture ends 144, 146 against the first surgically relevant object 22 will tend to compress the first and second surgically relevant objects 22, 36 against the pressure sensor 24, thereby creating a pressure which can be sensed by the pressure sensor 24.

As shown in FIG. 6A-1, the suture clamp 118 is positioned to allow sutures 145, 147 to be pulled through the guide block 152, the second surgically relevant object 36, the pressure sensor 24, and the first surgically relevant object 22. Even if the first and second suture ends 144, 146 had previously been used to tie a knot, when the clamp 118 is released from the sutures as shown in FIG. 6A-1, the knotted end could be pulled away from the frame and trimmed off to result in two fresh new suture ends 144, 146 so that a new knot may be tied once the clamp 118 is locked back in place.

Figures 1, 6B:
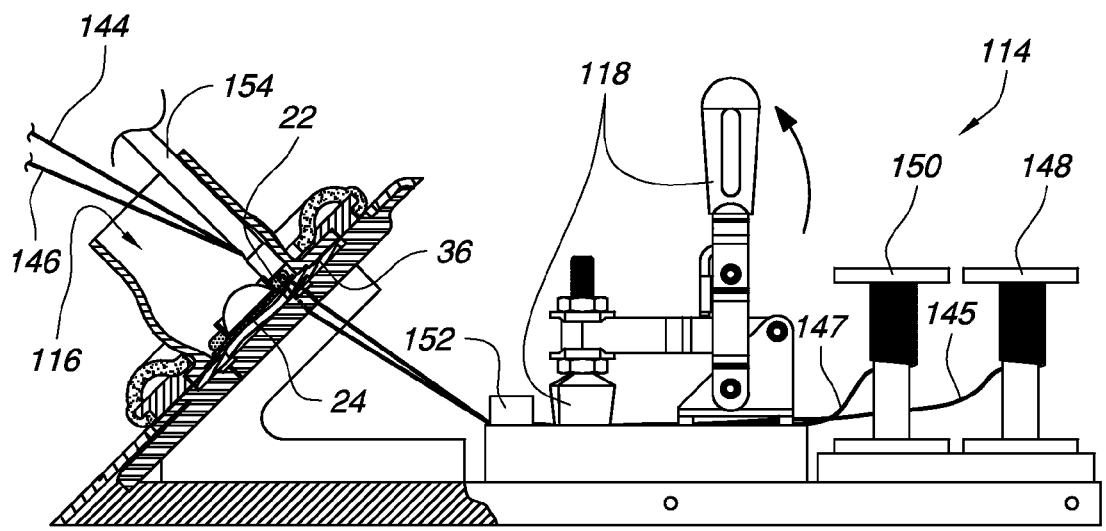
Figures 2, 6B:
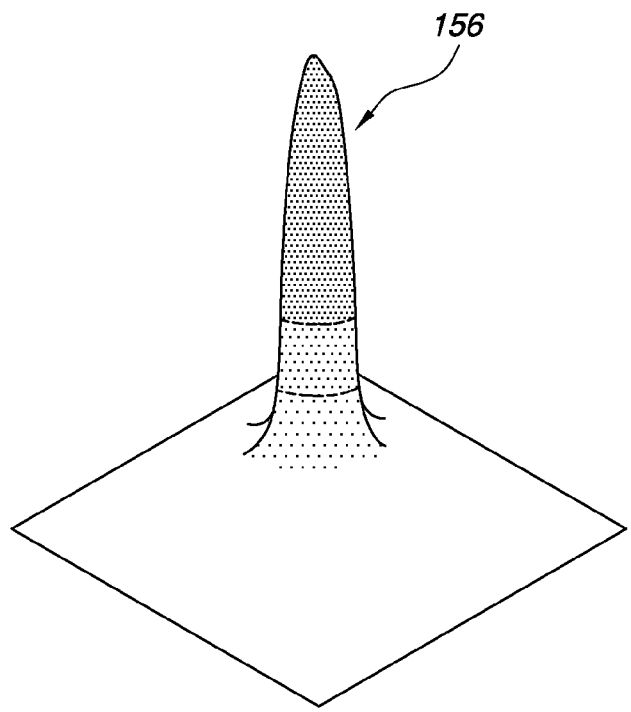

FIG. 6B-1 is a partial cross-sectional side view of the frame 114 from FIG. 6A-1 with the clamp 118 positioned to hold the sutures in place behind the one or more surgically relevant objects 22, 36 and the pressure sensor 24 while a mechanical knot is applied to the suture ends by minimally invasive fastening device 154. One non-limiting example of a fastening device 154 is the COR-KNOT® device manufactured and sold by LSI Solutions, Inc. of Victor, N.Y. (See www.lsisolutions.com). In the case of the COR-KNOT® device, the suture ends 144, 146 are snared through the end of the fastening device 154. Tension is applied to the suture ends 144, 146 and the surgeon activates the fastening device 154 to crimp a titanium knot onto the suture ends 144, 146 against the first surgically relevant object 22. FIG. 6B-2 schematically illustrates one embodiment of a three-dimensional (3D) pressure map associated with a location where the mechanical knot is being placed against one of the surgically relevant objects from FIG. 6B-1. Before the surgeon activates the fastening device 154, the combination of the surgeon pushing the end of the device 154 against the first surgically relevant object 22 and the tensioning of the suture ends 144, 146 will create a corresponding pressure spike 156 on the pressure map displayed on a user interface, as shown in FIG. 6B-2. A surgeon can look at this type of pressure map to help adjust the tension to a desired pressure prior to crimping the mechanical knot. Such information, when used in real-time, can help surgeons to set a desirable pressure for the knot as well as help surgeons create multiple related knots of similar pressures so that adjacent knots, for example, provide a balanced load to the underlying tissue and/or prosthesis.

Figures 1, 6C:
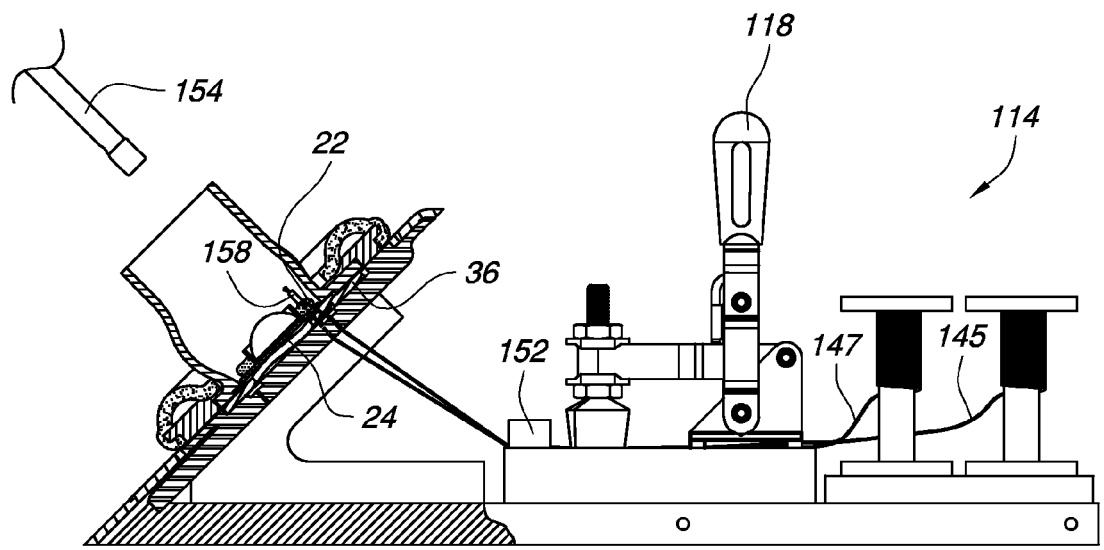
Figures 2, 6C:
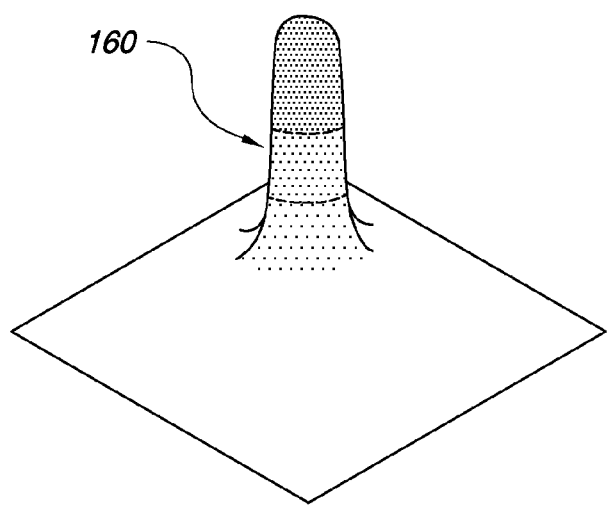

FIG. 6C-1 is a partial cross-sectional side view of the frame 114 from FIG. 6B-1 with the minimally invasive fastening device 154 removed after a mechanical fastener 158 has been applied to the suture ends. In this example, the surgeon decided to lower the tension from the pre-crimping level shown in FIG. 6B-2 before crimping the mechanical knot 158. FIG. 6C-2 schematically illustrates one embodiment of a 3D pressure map associated with the location where the mechanical knot was placed against the surgically relevant objects as shown in FIG. 6C-1. The corresponding pressure spike 160 has a lower magnitude than that of FIG. 6B-1.

In addition to using the systems described herein with mechanical knot tying methods, the systems for evaluating surgical knot formation are also quite useful in conjunction with hand tying of knots. Accordingly, FIGS. 7A-7L schematically illustrate a sample set of steps for forming a hand-tied surgical knot on a system for evaluating surgical knot formation. Each of the FIGS. 7A-7L also includes a 3D pressure map and a plot of pressure at the given knot location as a function of time. Items like the 3D pressure map and the plot of pressure at a given knot location can be displayed on an appropriate user interface. The hand knot tying process illustrated throughout FIGS. 7A-7L is a potential example of a set of data from an inexperienced surgical student who has the basic motions required to form an overhand knot memorized but who lacks the refinements and practice necessary to produce a suitably tensioned knot. The system, as indicated by the sample user interface displays, captures some insights into the causes of the poorly tensioned knots. In addition to the sample user interface display elements, for convenience, only the second surgically relevant object 36, the pressure sensor 24, the first surgically relevant object 22, and the suture ends 162, 164 passing through them are illustrated in FIGS. 7A-7L. It should be understood, however, that the system would have more elements, for example as described in the previous embodiments.

Figure 7A:
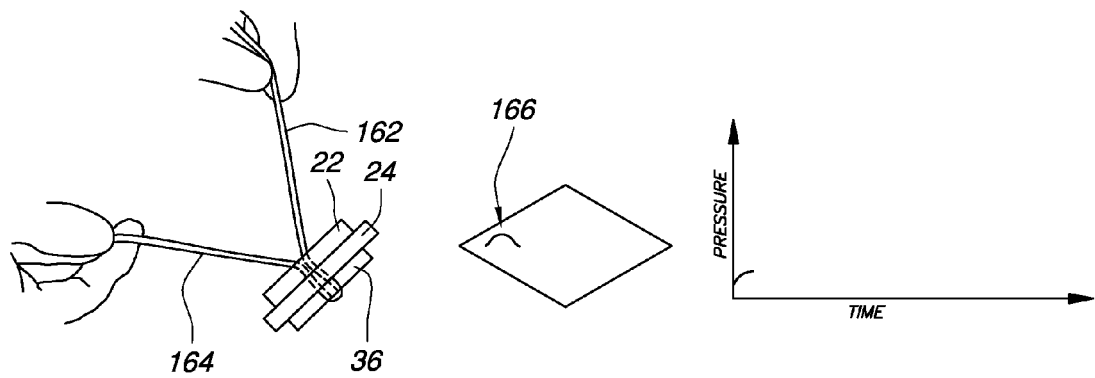
FIGS. 7A-7L schematically illustrate a sample set of steps for forming a hand-tied surgical knot on a system for evaluating surgical knot formation. Each of the FIGS. 7A-7L also includes a 3D pressure map and a plot of pressure at the given knot location as a function of time.

FIG. 7A illustrates an initial stage where the first and second suture ends 162, 164 are held by the student in preparation for forming the first throw of a square knot. The student was applying a light tension to the suture ends 162, 164, which pulled the second surgically relevant object 36 against the pressure sensor causing a corresponding pressure bump 166 to appear on the 3D pressure map. The pressure for that location on the pressure map is also being plotted over time in FIG. 7A.

Figure 7B:
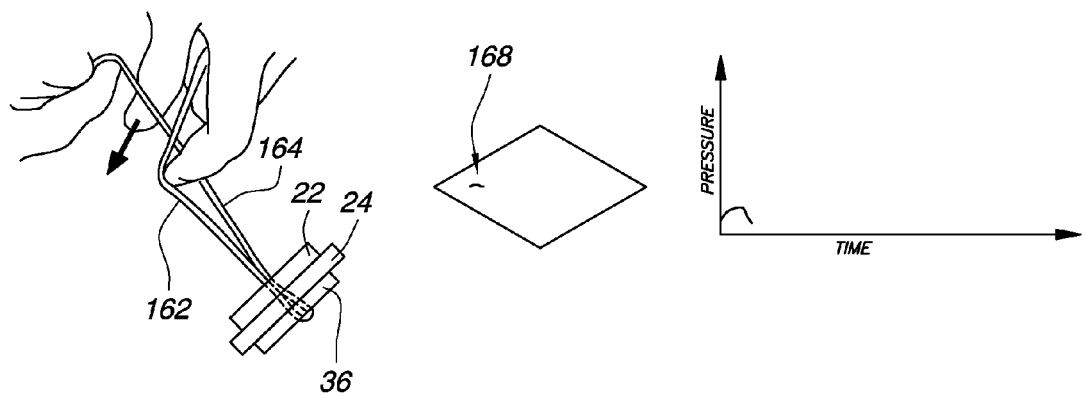

In FIG. 7B, a first loop is formed by the tip of the left index finger that passes its suture end 162 over the other suture end 164 held by the right hand. The left thumb also passes under the suture 164 held by the right hand. The suture end 162 slipped a little in the student's hand while performing this move, and the resultant pressure on the pressure sensor 24 went down as shown by the corresponding pressure "bump" 168 appearing on the 3D pressure map of FIG. 7B. As before, the pressure for that location on the pressure map is also being plotted over time in FIG. 7B, so the drop in pressure is also evident there.

Figure 7C:
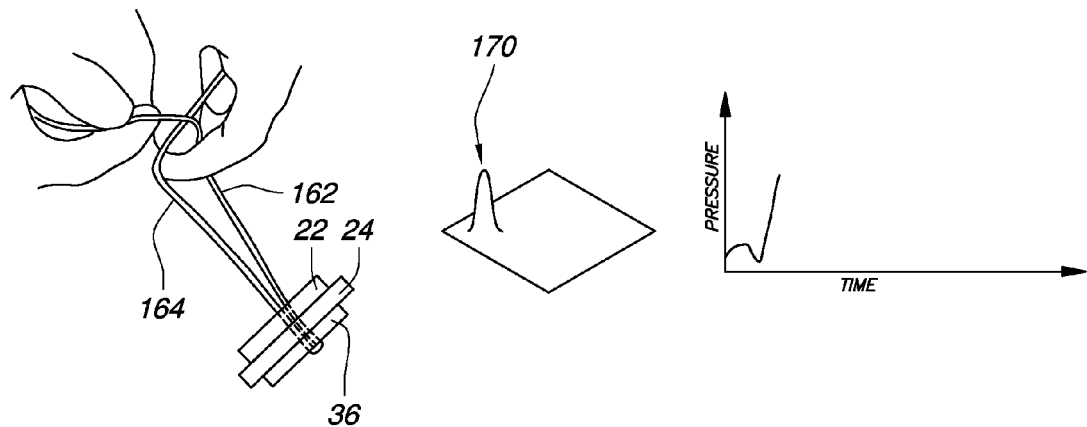

In FIG. 7C, the tip of the left thumb advances up through the suture loop, replacing the tip of the left index finger. The student realized that they had lost tension in the previous step and overcompensated during this step by pulling very hard on the sutures, using the left thumb as a fulcrum. The resultant pressure on the pressure sensor 24 increased rapidly as shown by the corresponding pressure bump 170 appearing on the 3D pressure map of FIG. 7C. The pressure for that location on the pressure map is also being plotted over time in FIG. 7C, so the rapid rise in pressure/tension is also very noticeable.

Figure 7D:
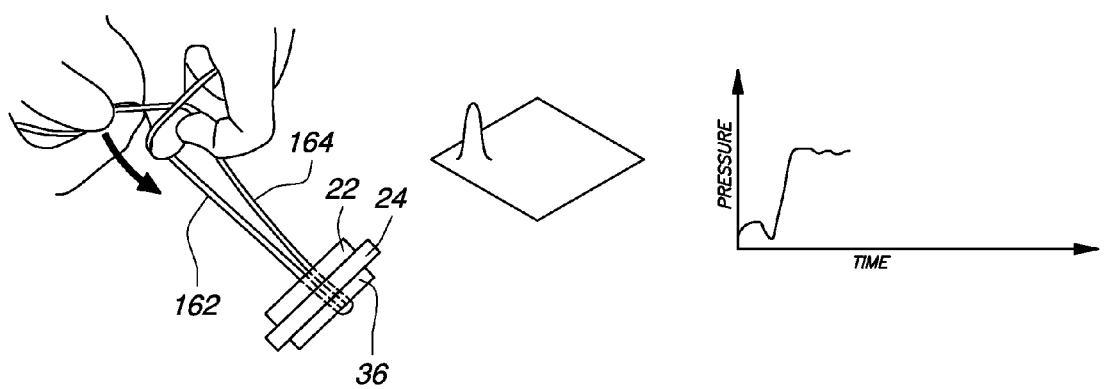

In FIG. 7D, the free suture end 164 held by the right hand is passed over the suture loop. The student had no trouble maintaining a similar pressure during this step, but the move did take a little longer than is ideal. The associated data displays of FIG. 7D illustrate this.

Figure 7E:
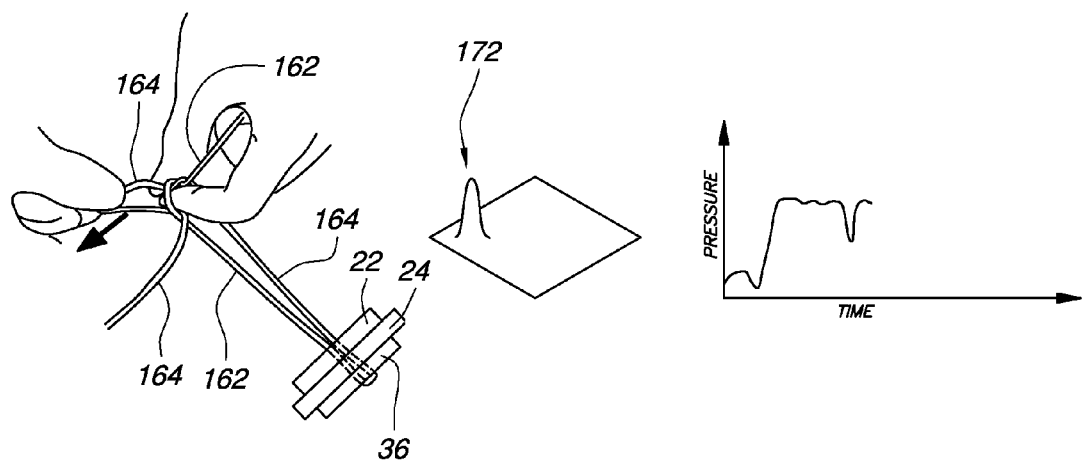

In FIG. 7E, the suture end 164 is grasped between the tips of the left thumb and index finger and passed downward through the suture loop. The right hand releases its free suture end so that it can be passed down through the suture loop. The free suture end 164 is regrasped between the tips of the right thumb and index finger to withdraw it through the suture loop to form a single wrap throw. The student momentarily lost tension on the sutures while regrasping the suture end 164. The resultant pressure on the pressure sensor 24 ended up close to where it had been previously as shown by corresponding pressure bump 172, but the graph of pressure versus time for that location on the pressure sensor clearly indicates the fluctuation in pressure as shown in FIG. 7E.

Figure 7F:
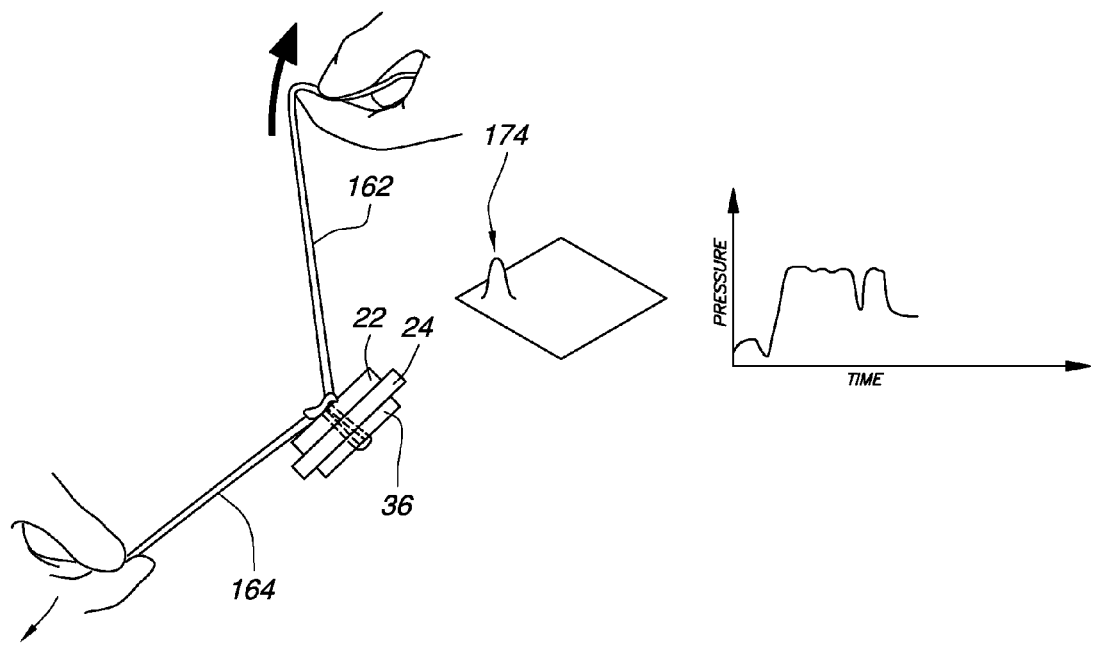

In FIG. 7F, the suture ends 162, 164 are grasped in the palms of the hands, the tips of the index fingers and thumbs position the suture ends 162, 164 at a desired orientation relative to the first surgically relevant object 22. Ideally, a constant tension should be applied to the suture ends to advance the first single-wrap throw of the square knot against the first surgically relevant object 22. The student tried for constant tension, but ended up pulling unevenly and very lightly on the suture ends 162, 164, resulting in a noticeable decrease in tension as shown by corresponding pressure bump 174 and the pressure versus time graph for that location in FIG. 7F.

Figure 7G:
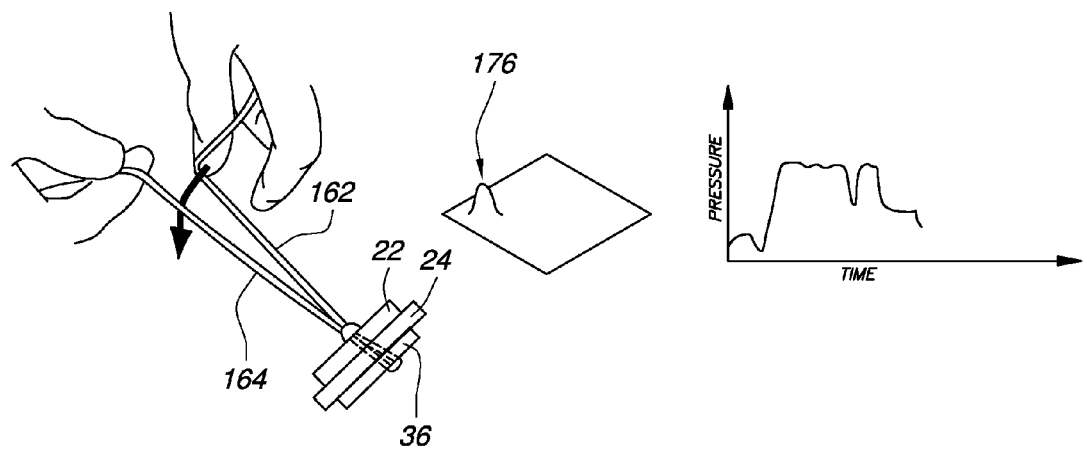

In FIG. 7G, the tip of the left thumb is passed under its suture end 162 in order to direct it beneath the other suture 164 that is held by the right hand. The student did not have a good grip of the suture end 162 in the left palm, so when the left hand released the grip of suture 162 from between the thumb and index finger, the student lost tension on the knot for a moment and then regained tension at a lower level than before the slip. The resultant pressure on pressure sensor 24 fell as indicated by corresponding pressure bump 176 and the pressure versus time graph for that location shown in FIG. 7G.

Figure 7H:
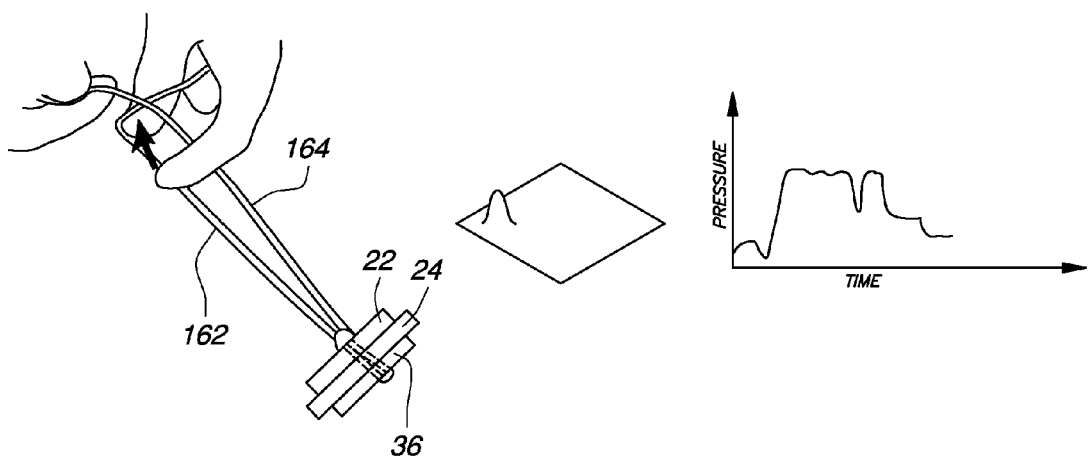

In FIG. 7H, the left thumb advances its suture end 162 beneath the other suture end 164 to form a suture loop. The tip of the left index finger passes down to touch the left thumb. The student maintained the previous tension during this maneuver. The associated data displays of FIG. 7H illustrate this.

Figure 7I:
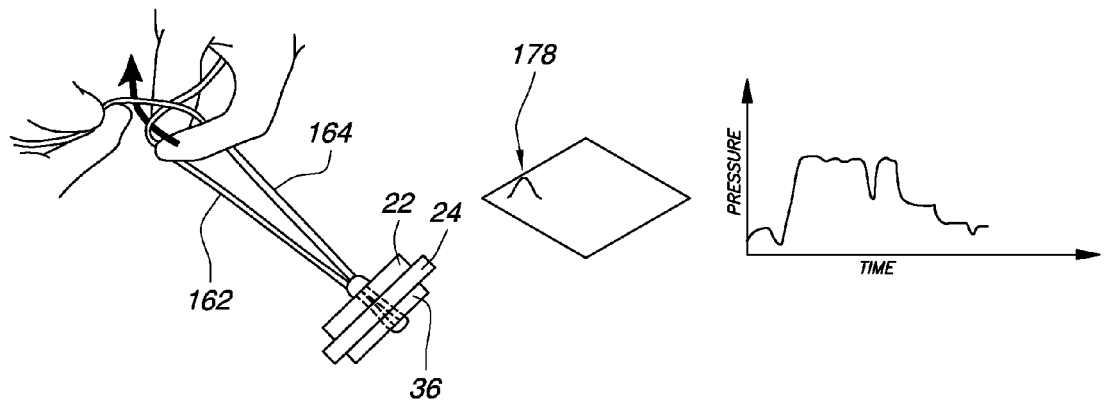

In FIG. 7I, after the tip of the left finger contacts the tip of the left thumb, both are pulled back through the suture loop so that only the tip of the left index finger remains in the loop. The student momentarily lost tension on the suture end 162 during the transition from the left thumb to the left index finger pressing against suture end 162. The resultant pressure on pressure sensor 24 dropped momentarily and then was resumed at a slightly lower level as shown with corresponding pressure bump 178 and the pressure versus time graph for that location shown in FIG. 7I.

Figure 7J:
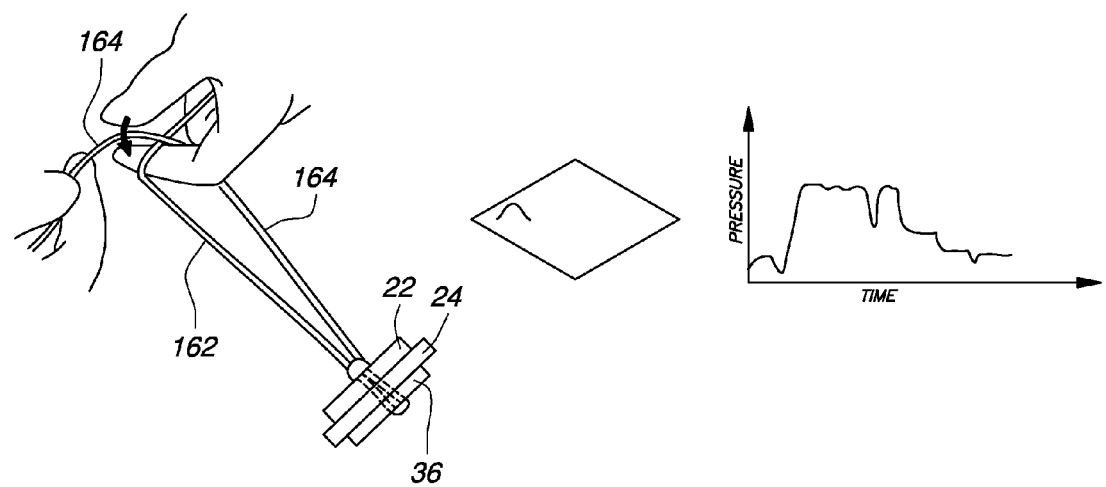

In FIG. 7J, the free suture end 164 held by the right hand is passed under the suture loop to be positioned between the tips of the left index finger and thumb. The student maintained tension during this step as illustrated in the associated data displays of FIG. 7J.

Figure 7K:
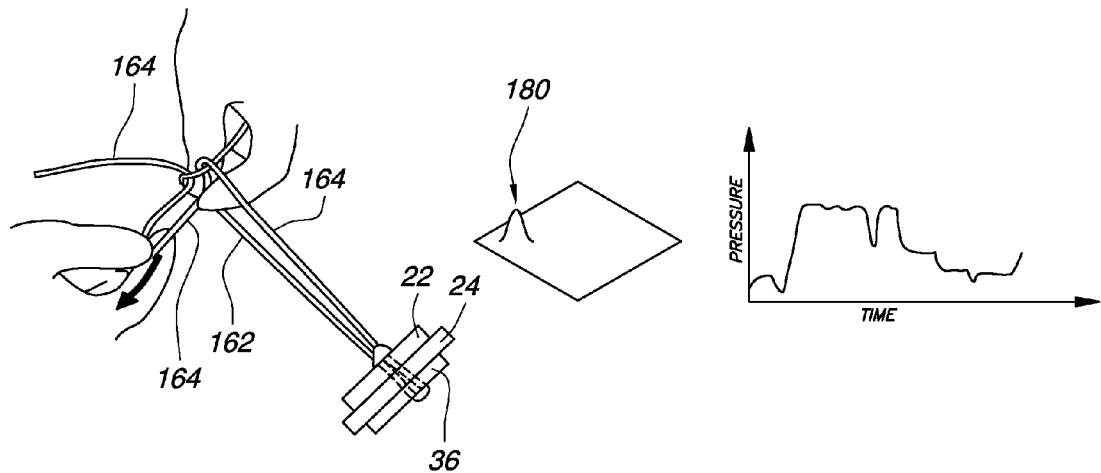

In FIG. 7K, the free suture end 164 grasped between the tips of the left thumb and index finger is advanced upward through the suture loop. The right hand releases its free suture end 164 to allow its passage through the suture loop, after which it regrasps the free suture end 164 to withdraw through the suture loop. The student started to wonder if the suture was pulled tightly enough, so more tension was applied to the suture ends during this step. The resultant pressure on pressure sensor 24 increased as indicated by corresponding pressure bump 180 and the pressure versus time graph for that location shown in FIG. 7K.

Figure 7L:
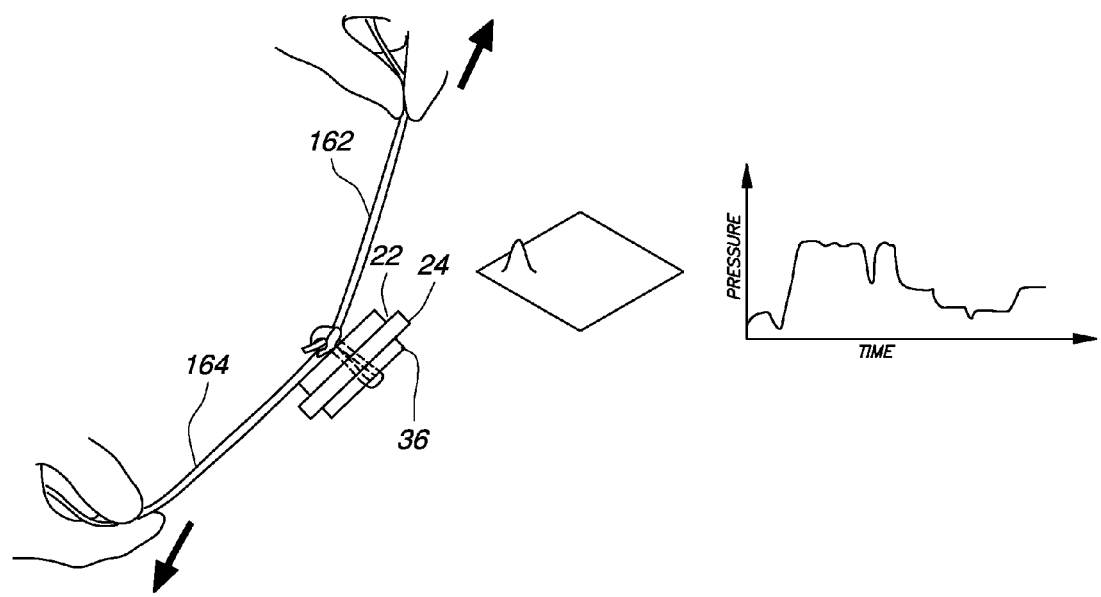

Finally, in FIG. 7L, the second throw is advanced and set against the first throw by applying tension at a desired orientation relative to the first surgically relevant object 22. The student was able to keep tension constant during this step to finish the knot. This is illustrated in the associated data displays of FIG. 7L.

Figure 8A:
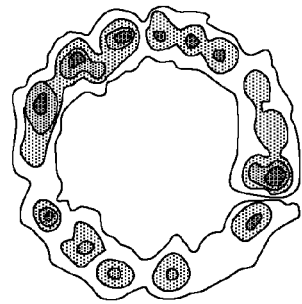
FIG. 8A is a 2D pressure map, resultant from attaching an aortic valve sewing ring to a simulated aortic root with multiple hand-tied suture knots, as may be determined by a system for evaluating surgical knot formation.
Figure 8B:
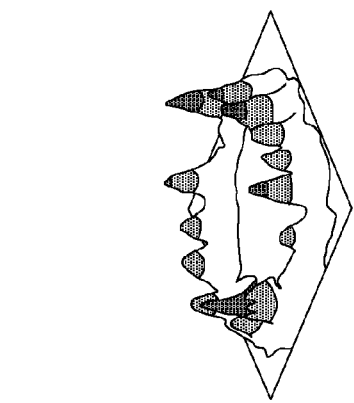
FIG. 8B is a 3D pressure map corresponding to the 2D pressure map of FIG. 8A.
Figure 8C:
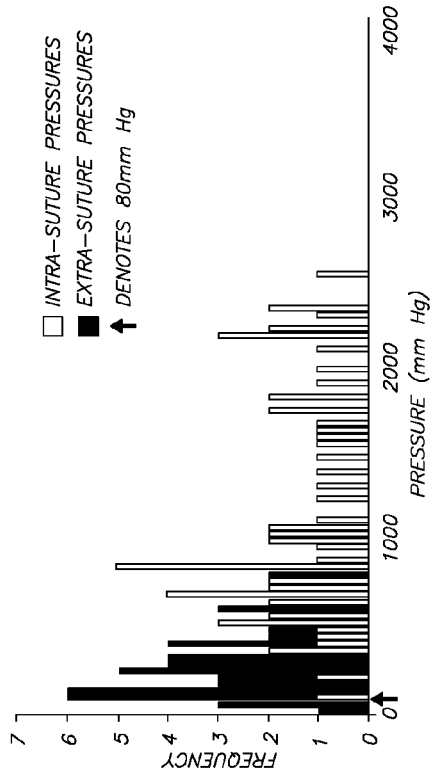
FIG. 8C is an embodiment of a histogram of intraknot and extraknot pressures resultant from attaching an aortic valve sewing ring to a simulated aortic root with multiple hand-tied suture knots, as may be determined by a system for evaluating surgical knot formation.

For simplicity of explanation, the embodiments illustrated up to this point have been concerned with the evaluation of a single knot. As noted previously, however, the systems and methods for evaluating surgical knot formation described herein, and their equivalents, are also ideally suited for evaluation of multiple knots. As one example, FIG. 8A is a 2D pressure map, resultant from attaching an aortic valve sewing ring to a simulated aortic root with multiple hand-tied suture knots, as may be generated by a system for evaluating surgical knot formation, such as those disclosed herein. FIG. 8B is a 3D pressure map corresponding to the 2D pressure map of FIG. 8A. In this hand-tied example, there was considerable variability in knot tension as well as several knots with tensions lower than a desirable minimum level. FIG. 8C is an embodiment of a histogram of intraknot and extraknot pressures resultant from attaching an aortic valve sewing ring to a simulated aortic root with multiple hand-tied suture knots, as may be determined by a system for evaluating surgical knot formation.

Figure 9A:
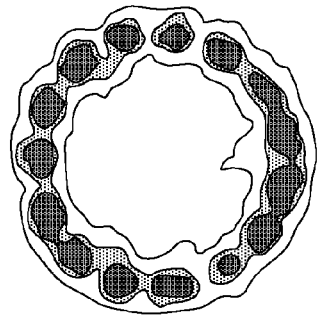
FIG. 9A is a two-dimensional (2D) pressure map, resultant from attaching an aortic valve sewing ring to a simulated aortic root with multiple suture end pairs held by a corresponding number of mechanical knots, as determined by a system for evaluating surgical knot formation.
Figure 9B:
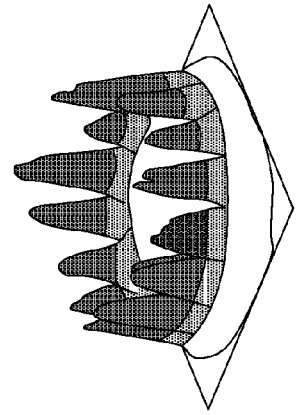
FIG. 9B is a 3D pressure map corresponding to the 2D pressure map of FIG. 9A.
Figure 9C:
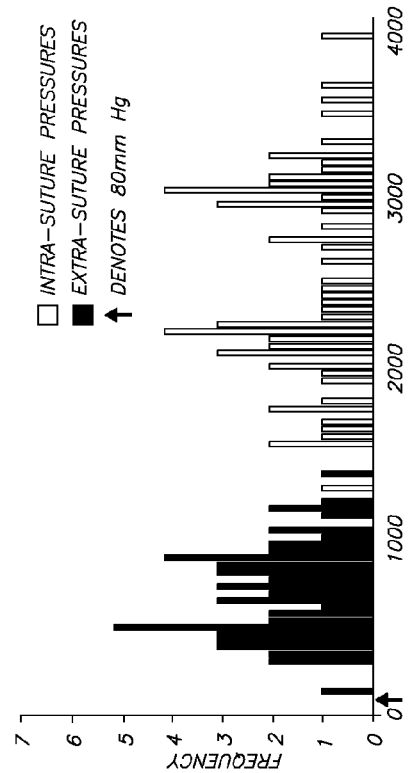
FIG. 9C is an embodiment of a histogram of intraknot and extraknot pressures, resultant from attaching an aortic valve sewing ring to a simulated aortic root with multiple suture end pairs held by a corresponding number of mechanical knots, as may be determined by a system for evaluating surgical knot formation.

As another multiple knot example, FIG. 9A is a two-dimensional (2D) pressure map, resultant from attaching an aortic valve sewing ring to a simulated aortic root with multiple suture end pairs held by a corresponding number of mechanical knots, as determined by a system for evaluating surgical knot formation, such as those disclosed herein. FIG. 9B is a 3D pressure map corresponding to the 2D pressure map of FIG. 9A. In this mechanical knot example, there was less variability in knot tension, with all knot tensions higher than a desirable minimum level. FIG. 9C is an embodiment of a histogram of intraknot and extraknot pressures, resultant from attaching an aortic valve sewing ring to a simulated aortic root with multiple suture end pairs held by a corresponding number of mechanical knots, as may be determined by a system for evaluating surgical knot formation.

Figure 10:
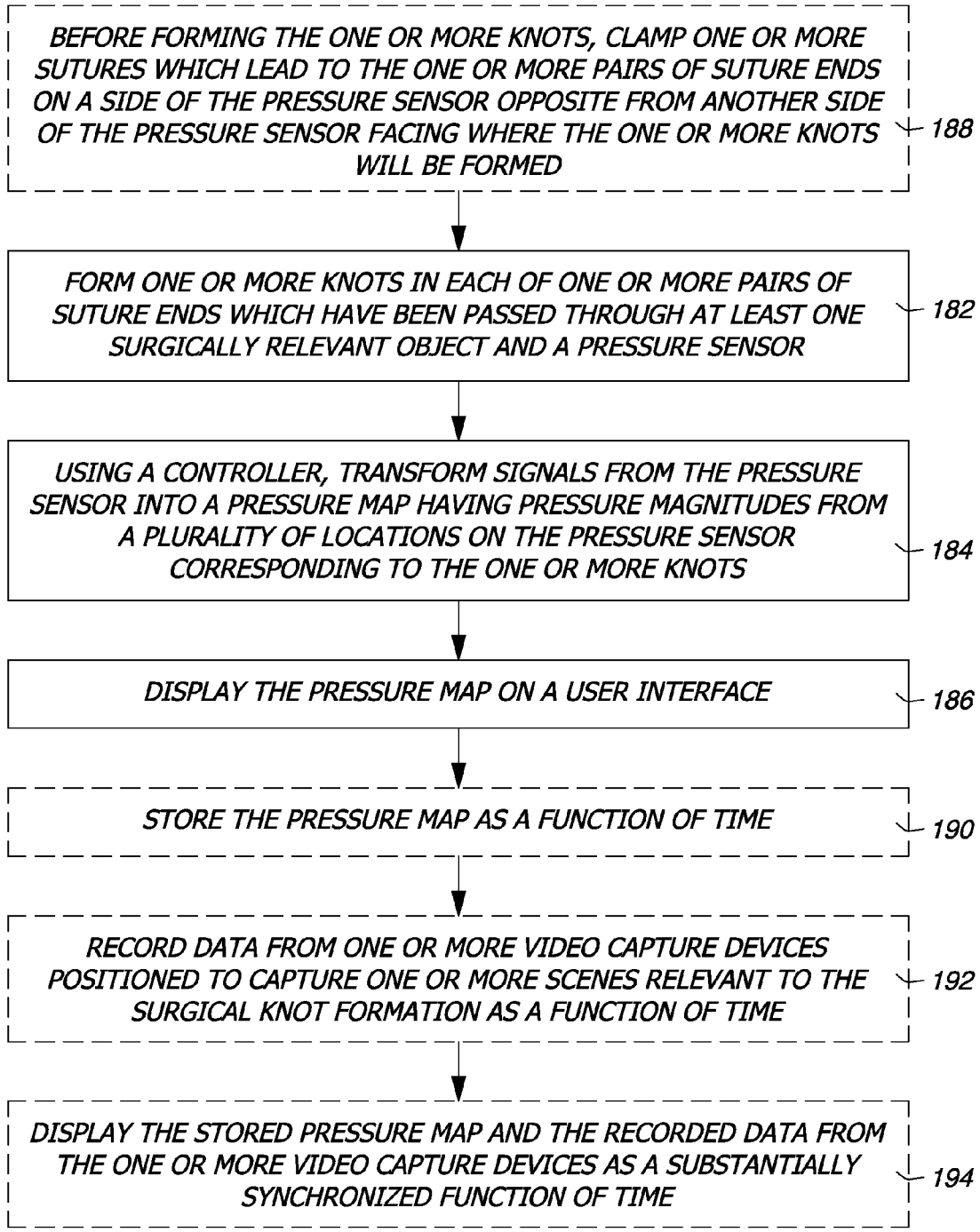
FIG. 10 illustrates one embodiment of a method for evaluating surgical knot formation.

FIG. 10 illustrates one embodiment of a method for evaluating surgical knot formation. In step 182, one or more knots are formed in each of one or more pairs of suture ends which have been passed through at least one surgically relevant object and a pressure sensor. Suitable examples of surgically relevant objects and pressure sensors have been discussed previously in this specification. Furthermore, the knots may be formed in a variety of ways, including, but not limited to hand tying and application of mechanical knots. In step 184, using a controller, signals from the pressure sensor are transformed into a pressure map having pressure magnitudes from a plurality of locations on the pressure sensor corresponding to the one or more knots. Suitable examples of a controller have been discussed previously. In step 186, the pressure map is displayed on a user interface. Suitable examples of both a user interface, as well as a variety of non-limiting examples for displaying a pressure map have been discussed previously.

Optionally, in step 188, before forming the one or more knots, one or more sutures which lead to the one or more pairs of suture ends are clamped on a side of the pressure sensor opposite from another side of the pressure sensor facing where the one or more knots will be formed.

Optionally, in step 190, the pressure map may be stored as a function of time.

Optionally, in step 192, data from one or more video capture devices positioned to capture one or more scenes relevant to the surgical knot formation may be captured as a function of time.

Optionally, in step 194, the stored pressure map and the recorded data from the one or more video capture devices are displayed as a substantially synchronized function of time.

Various advantages of a system and method for evaluating surgical knot formation have been discussed above. The disclosed systems, methods, and their equivalents provide surgeons with the ability to objectively assess knot-tying results while allowing for immediate critical feedback on technique. Data from accomplished cardiac surgeons can be integrated to provide students with quantitative references that compare their skills to others. Similar comparisons and benchmarks may be established for a wide variety of surgical fields. Furthermore, the disclosed systems, methods, and their equivalents enable students and trainees to reach the highest standards required of them without endangering patient care.

Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A system for evaluating surgical knot formation, comprising:
    a) a first surgically relevant object;
    b) a pressure sensor;
    c) at least one pair of suture ends passing through the pressure sensor and the first surgically relevant object; and
    d) a controller coupled to the pressure sensor and configured to:
        1) transform signals from the pressure sensor into a pressure map having pressure magnitudes from a plurality of locations on the pressure sensor corresponding to one or more knots which may be formed in the at least one pair of suture ends; and
        2) format the pressure map for display.

2. The system of claim 1, wherein the first surgically relevant object is selected from the group consisting of a synthetic tissue, a tissue, a cardiac prosthesis, and a prosthetic surgical material.

3. The system of claim 1, further comprising a second surgically relevant object, and wherein the at least one pair of suture ends passes through the second surgically relevant object, the pressure sensor, and the first surgically relevant object.

4. The system of claim 3, further comprising:
    a frame configured to support at least one of the first surgically relevant object, the pressure sensor, or the second surgically relevant object.

5. The system of claim 3, wherein the second surgically relevant object is selected from the group consisting of a synthetic tissue, a tissue, and an aortic root model.

6. The system of claim 1, wherein the at least one pair of suture ends comprises:
    a first end of a first suture; and
    a first end of a second suture.

7. The system of claim 6, wherein:
    the first suture comprises a second end having an anchor; and
    the second suture comprises a second end having an anchor.

8. The system of claim 6, wherein:
    the first suture comprises a second end wrapped around a first spool; and
    the second suture comprises a second end wrapped around a second spool.

9. The system of claim 8, wherein the first and second spools are selectively lockable to prevent rotation of the spools and payout of the first and second sutures while locked.

10. The system of claim 8, further comprising at least one clamp to selectively lock the second end of the first suture and the second end of the second suture in place.

11. The system of claim 1, wherein the at least one pair of suture ends comprise first and second ends of a same suture.

12. The system of claim 11, wherein the first and second suture ends pass through a pledget before passing through the pressure sensor and the first surgically relevant object.

13. The system of claim 1, further comprising:
    a frame configured to support at least one of the first surgically relevant object or the pressure sensor.

14. The system of claim 1 wherein the controller is wirelessly coupled to the pressure sensor.

15. The system of claim 1, further comprising a user interface coupled to the controller, and wherein the controller is further configured to display the pressure map on the user interface.

16. The system of claim 1, further comprising a database coupled to the controller.

17. The system of claim 1, further comprising at least one video capture device coupled to the controller.

18. The system of claim 17, wherein the at least one video capture device comprises:
    a first video capture device configured, in conjunction with the controller, to record a surgeon's hands while said hands are directly or indirectly manipulating the at least one pair of suture ends to form a knot against the first surgically relevant object; and
    a second video capture device configured to record, in conjunction with the controller, the surgeon's face.

19. The system of claim 18, wherein the at least one video capture device further comprises:
   a third video capture device configured to record, in conjunction with the controller, the knot being formed against the first surgically relevant object.

20. The system of claim 1, wherein the first surgically relevant object comprises the pressure sensor.

21. A system for evaluating surgical knot formation, comprising:
   a) a pressure sensor configured to be held in conjunction with a first surgically relevant object and/or a second surgically relevant object by:
      1) passage of at least one pair of suture ends through the pressure sensor and the first surgically relevant object; or
      2) passage of the at least one pair of suture ends through the second surgically relevant object, the pressure sensor, and the first surgically relevant object; and
   b) a controller coupled to the pressure sensor and configured to:
      1) transform signals from the pressure sensor into a pressure map having pressure magnitudes from a plurality of locations on the pressure sensor corresponding to one or more knots which may be formed in the at least one pair of suture ends; and
      2) format the pressure map for display.

22. A method for evaluating surgical knot formation, comprising:
   forming one or more knots in each of one or more pairs of suture ends which have been passed through at least one surgically relevant object and a pressure sensor;
   using a controller, transforming signals from the pressure sensor into a pressure map having pressure magnitudes from a plurality of locations on the pressure sensor corresponding to the one or more or more knots; and
   displaying the pressure map on a user interface.

23. The method of 22, wherein forming the one or more knots in each of the one or more pairs of suture ends comprises hand-tying the one or more knots.

24. The method of 22, wherein forming the one or more knots in each of the one or more pairs of suture ends comprises using a fastening apparatus to fasten one or more mechanical fasteners as mechanical knots to secure the one or more pairs of suture ends.

25. The method of 22, wherein displaying the pressure map on the user interface comprises displaying a time-varying three dimensional pressure map.

26. The method of 22, wherein displaying the pressure map on the user interface comprises displaying a time-varying two-dimensional pressure map.

27. The method of 22, wherein displaying the pressure map on a user interface comprises plotting a pressure at a given location corresponding to at least one of the one or more knots as a function of time.

28. The method of 22, wherein displaying the pressure map on a user interface comprises displaying a two-dimensional pressure map.

29. The method of 22, wherein displaying the pressure map on a user interface comprises displaying a three-dimensional pressure map.

30. The method of 22, wherein displaying the pressure map on a user interface comprises displaying a histogram of intraknot and/or extraknot pressures.

31. The method of 22, further comprising:
   storing the pressure map as a function of time; and
   recording data from one or more video capture devices positioned to capture one or more scenes relevant to the surgical knot formation as a function of time.

32. The method of 31, further comprising:
   displaying the stored pressure map and the recorded data from the one or more video capture devices as a substantially synchronized function of time.

33. The method of 31, wherein the one or more scenes relevant to the surgical knot formation comprise:
   at least a portion of the face of a person who is forming the one or more knots.

34. The method of 31, wherein the one or more scenes relevant to the surgical knot formation comprise:
   at least a portion of the hands of a person who is forming the one or more knots.

35. The method of 31, wherein the one or more scenes relevant to the surgical knot formation comprise:
   an area where the one or more knots are being formed.

36. The method of claim 22, further comprising:
   before forming the one or more knots, clamping one or more sutures which lead to the one or more pairs of suture ends on a side of the pressure sensor opposite from another side of the pressure sensor facing where the one or more knots will be formed.

37. The method of claim 22, wherein said forming one or more knots in each of one or more pairs of suture ends comprises adjusting a knot tension based on feedback from the pressure map displayed on the user interface.

* * * * *